United States Patent [19]

Taylor et al.

[11] Patent Number: 5,702,389
[45] Date of Patent: Dec. 30, 1997

[54] ORTHOPAEDIC FIXATION DEVICE

[75] Inventors: Harold S. Taylor; J. Charles Taylor, both of Memphis, Tenn.

[73] Assignee: Smith & Nephew Richards, Inc., Memphis, Tenn.

[21] Appl. No.: 782,731

[22] Filed: Jan. 13, 1997

Related U.S. Application Data

[63] Continuation of Ser. No. 396,624, Mar. 1, 1995, abandoned.

[51] Int. Cl.$^6$ ................................. A61B 17/60
[52] U.S. Cl. .................... 606/54; 606/56; 606/57; 606/59
[58] Field of Search ............... 606/54, 55, 56, 606/57, 58, 59, 60, 61; 402/122, 170, 169, 217

[56] References Cited

U.S. PATENT DOCUMENTS

| | | | |
|---|---|---|---|
| 1,308,799 | 7/1919 | Masland . | |
| 2,055,024 | 9/1936 | Bittner, Jr. | 128/85 |
| 2,250,417 | 7/1941 | Ettinger . | |
| 2,391,537 | 12/1945 | Anderson . | |
| 2,487,989 | 11/1949 | Sherburne | 287/88 |
| 3,176,805 | 4/1965 | Gandy | 189/28 |
| 3,727,610 | 4/1973 | Riniker | 128/92 A |
| 3,941,123 | 3/1976 | Volkov et al. . | |
| 3,977,397 | 8/1976 | Kalnberz et al. | 128/92 A |
| 4,033,340 | 7/1977 | Kalnberz . | |
| 4,100,919 | 7/1978 | Oganesyan et al. . | |
| 4,112,935 | 9/1978 | Latypov et al. | 606/61 |
| 4,308,863 | 1/1982 | Fischer | 128/92 A |

(List continued on next page.)

FOREIGN PATENT DOCUMENTS

| | | | |
|---|---|---|---|
| 0 589 565 | 3/1994 | European Pat. Off. | B23Q 1/02 |
| 25 46 046 | 4/1977 | Germany . | |
| 820813 | 4/1981 | U.S.S.R. | A61B 17/18 |
| 1 255 118 | 9/1986 | U.S.S.R. | A61B 17/58 |
| 108119 | 7/1917 | United Kingdom . | |
| 2 077 847 | 12/1981 | United Kingdom . | |
| WO 91/06253 | 5/1991 | WIPO | A61B 17/60 |
| WO 92/17313 | 10/1992 | WIPO | B23Q 1/14 |

OTHER PUBLICATIONS

The Ilizarov Method Bioskills Workshop Handbook, Essential Concepts & Methodology for Application of the Ilizarov Technique, 26 pages.

Geng, Z.J., Haynes, L.S., "A 3-2-1' Kinematic Configuration Of A Stewart Platform And Its Application to Six Degree Of Freedom Pose Measurements", *Robotics & Computer–Integrated Manufacturing*, vol. 11, No. 1, 1994, pp. 23–34.

(List continued on next page.)

*Primary Examiner*—Michael Buiz
*Assistant Examiner*—Daphna Shai
*Attorney, Agent, or Firm*—Earl M. Douglas; Larry McKenzie

[57] ABSTRACT

A spatial frame for positioning a first element or the like relative to a second element or the like. The spatial frame includes a first base for mounting to the first element; a second base for mounting to the second element; a plurality of adjustable effective length struts; connector structure for rotatably attaching the first ends of a first pair of struts relative to one another and relative to the first base; connector structure for rotatably attaching the first ends of a second pair of struts relative to one another and relative to the first base; connector structure for rotatably attaching the first ends of a third pair of struts relative to one another and relative to the first base; connector structure for rotatably attaching the second ends of the first pair of struts relative to one another and relative to the second base; connector structure for rotatably attaching the second ends of the second pair of struts relative to one another and relative to the second base member; and connector structure for rotatably attaching the second ends of the third pair of struts relative to one another and relative to the second base member.

30 Claims, 9 Drawing Sheets

U.S. PATENT DOCUMENTS

| | | |
|---|---|---|
| 4,361,144 | 11/1982 | Slätis et al. |
| 4,482,266 | 11/1984 | Kaneko .................................. 128/135 |
| 4,483,334 | 11/1984 | Murray. |
| 4,502,473 | 3/1985 | Harris et al. ........................... 128/91 A |
| 4,541,422 | 9/1985 | de Zbikowski. |
| 4,570,625 | 2/1986 | Harris et al. ........................... 128/92 G |
| 4,615,338 | 10/1986 | Ilizarov et al. |
| 4,620,533 | 11/1986 | Mears. |
| 4,624,249 | 11/1986 | Alvarez Cambras .............. 128/92 ZK |
| 4,628,922 | 12/1986 | Dewar .................................. 128/92 Z |
| 4,662,365 | 5/1987 | Gotzen et al. |
| 4,768,524 | 9/1988 | Hardy .................................. 128/92 Z |
| 4,889,111 | 12/1989 | Ben-Dov. |
| 4,928,546 | 5/1990 | Walters ................................. 403/122 |
| 4,973,331 | 11/1990 | Pursley et al. ........................ 606/54 |
| 4,988,244 | 1/1991 | Sheldon et al. ....................... 409/132 |
| 5,028,180 | 7/1991 | Sheldon et al. ....................... 409/201 |
| 5,062,844 | 11/1991 | Jamison et al. ....................... 606/54 |
| 5,170,790 | 12/1992 | Lacoste et al. .................... 138/660.01 |
| 5,180,380 | 1/1993 | Pursley et al. ........................ 606/54 |
| 5,209,750 | 5/1993 | Stef ....................................... 606/54 |
| 5,259,710 | 11/1993 | Charles ................................. 409/235 |
| 5,275,598 | 1/1994 | Cook ..................................... 606/54 |
| 5,354,158 | 10/1994 | Sheldon et al. ....................... 409/201 |
| 5,388,935 | 2/1995 | Sheldon ................................ 409/201 |
| 5,405,347 | 4/1995 | Lee et al. .............................. 606/54 |
| 5,461,515 | 10/1995 | Sorce .................................... 359/872 |
| 5,466,085 | 11/1995 | Sheldon et al. ....................... 403/157 |
| 5,490,784 | 2/1996 | Carmein ................................ 434/55 |

OTHER PUBLICATIONS

Smith & Nephew Richards Inc., *The Original Ilizarov System, The Ilizarov External Fixator General Surgical Technique Brochure*, 1988.

Dasgupta, B., Mruthyunjaya, T.S., "A Canonical Formulation Of The Direct Position Kinematics Problem For A General 6–6 Stewart Platform", *Mech. Mach. Theory*, vol. 29, No. 6, 1994, pp.819–827.

Liu, K., Lewis, F.L., Fitzgerald, M., "Solution Of Nonlinear Kinematics Of A Parallel–Link Constrained Stewart Platform Manipulator", *Circuits System Signal Process*, vol. 13, No. 2–3, 1994, pp. 167–183.

Zhuang, H., Roth, Z.S., "Method For Kinematic Calibration Of Stewart Platforms", *Journal Of Robotic Systems*, 10(3), 1993, pp. 391–405.

Stoughton, R.S., Arai, T., "A Modified Sewart Platform Manipulator With Improved Dexterity", *IEEE Transactions On Robotics And Automation*, vol. 9, No. 2, Apr. 1993.

Wen, F., Liang, C., "Displacement Analysis Of The 6–6 Stewart Platform Mechanisms", *Mech. Mach Theory*, vol. 29, No. 4, 1994, pp. 547–557.

Zhang, C., Song, S., "Forward Position Analysis Of Nearly General Stewart Platforms", *Journal of Mechanical Design*, vol. 116, pp. 54–60, Mar. 1994.

Nair, R., Maddocks, J.H., "On The Forward Kinematics Of Parallel Manipulators", *The International Journal of Robotics Research*, vol. 13, No. 2, Apr. 1994, pp. 171–188.

Dasgupta, B., Mruthyunjaya, T.S., "Letter To The Editor", *Mech. Mach. Theory*, vol. 29, No. 2., 1994, p. 341.

Fenton, R.G., "Response", *Mech. Mach. Theory*, vol. 29, No. 2, 1994, p. 343.

Liu, K., Fitzgerald, J.M., Lewis, F.L., "Kinematic Analysis of a Stewart Platform Manipulator", *IEEE Transaction On Industrial Electronics*, vol. 40, No. 2, Apr. 1993, pp. 282–293.

Raghavan, M., "The Stewart Platform of General Geometry Has 40 Configurations", *Journal of Mechanical Design*, vol. 115, Jun. 1993, pp. 277–282.

Ji, Z., "Dynamics Decomposition for Stewart Platforms", *Journal of Mechanical Design*, vol. 116, Mar. 1994, pp. 67–69.

Chen, N., Song, S., "Direct Position Analysis of the 4–6 Stewart Platforms", *Journal of Mechanical Design*, vol. 116, Mar. 1994, pp. 61–66.

Wohlhart, K., "Displacement Analysis Of The General Spherical Stewart Platform", *Mech. Mach. Theory*, vol. 29, No. 4, 1994, pp. 581–589.

Catagni, M.A., Malzev, V., Kirienko, Al., *Advances In Ilizarov Apparatus Assembly*, 1994.

VARIAX™, Giddings & Lewis® Automation Technology, 4 pages.

S. V. Sreenivasan et al., "Closed–Form Direct Displacement Analysis of a 6–6 Stewart Platform," *Mech. Mach. Theory*, vol. 29, No. 6, pp. 855–864, 1994.

"Basic Ilizarov Techniques," *Techniques in Orthopaedics®*, vol. 5, No. 4, Dec. 1990, pp. 55–59.

Richards Medical Company, *Richards External Fixation Systems*, 1983, 8 pages.

Richards Medical Company, *The Ilizarov External Fixator General Technique Brochure*, 1988, cover and p. 17.

*Hex–Fix Surgical Technique* brochure, title page and pp. 1–7.

Pfizer Hospital Products Group, Inc. (Howmedica), *Monticelli Spinelli® External Fixation System*, 1991, cover and pages 1–28.

Nanua P, Waldron KJ, and Murthy V. "Direct Kinematic Solution of a Stewart Platform." IEEE Transactions on Robotics and Automation. 6:4, pp. 438–444, Aug. 1990.

Fichter EF. "A Stewart Platform–Based Manipulator: General Theory and Practical Construction." Internation Journal of Robotics Research. 5:2, pp. 157–182, 1986.

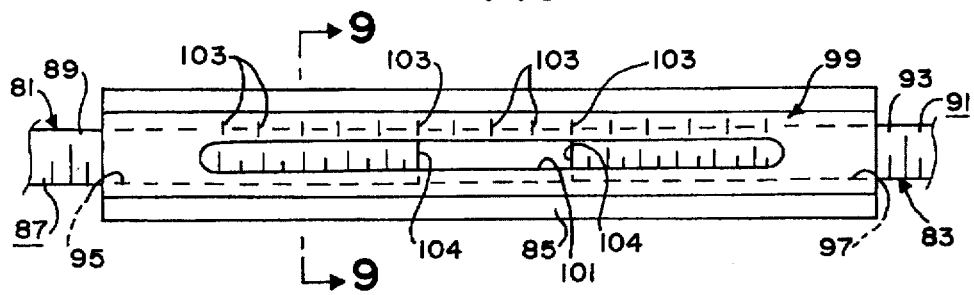
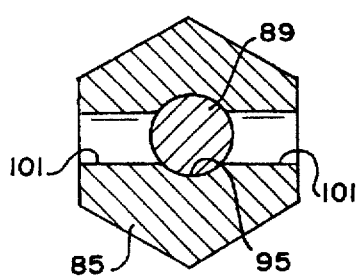
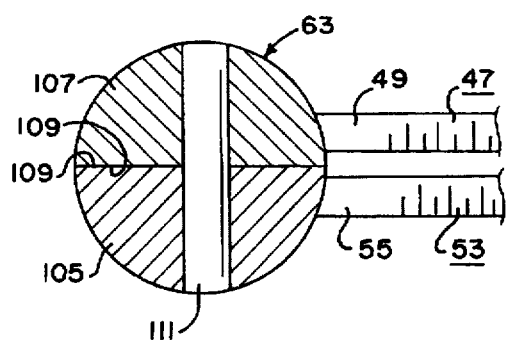
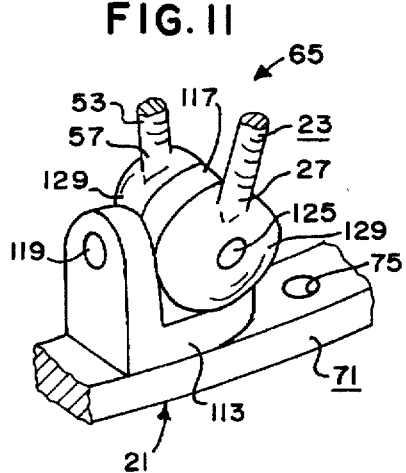
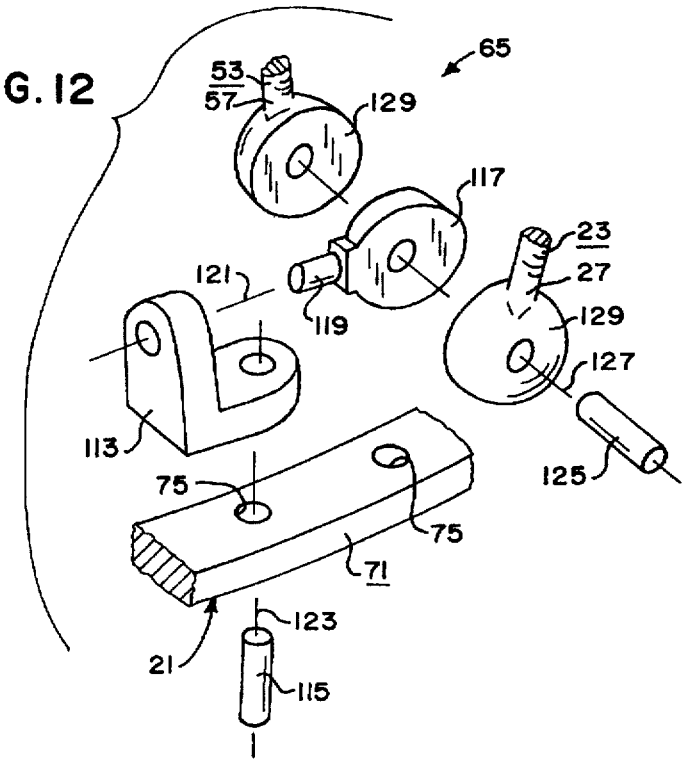

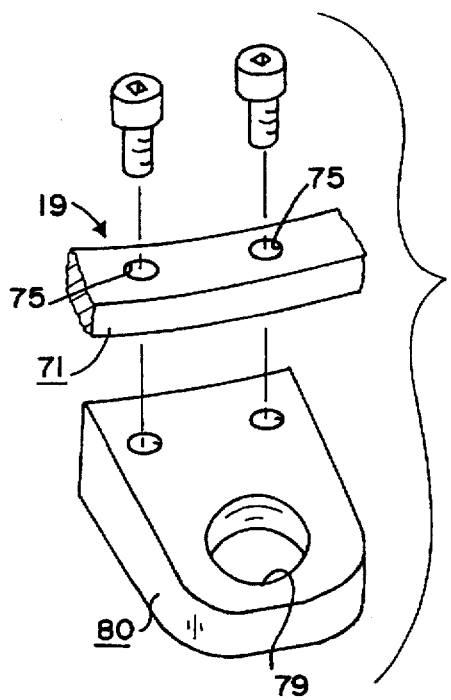
FIG. 25
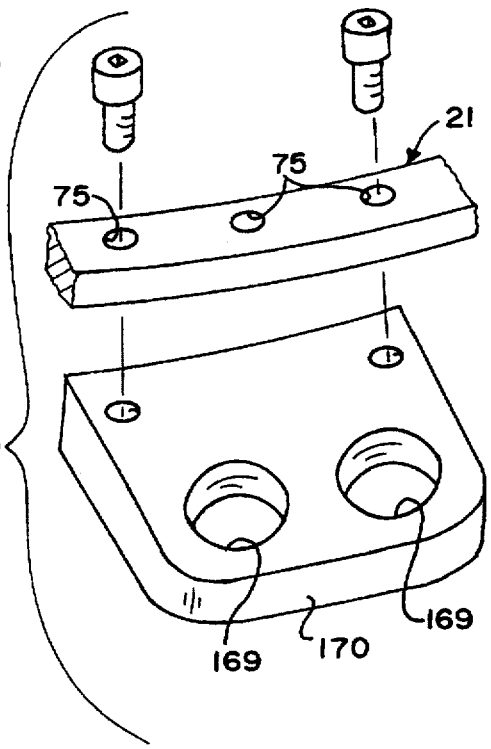
FIG. 26
FIG. 27
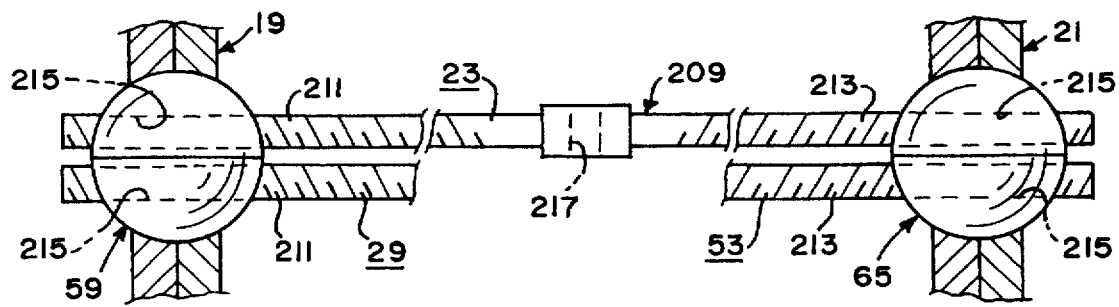

ORTHOPAEDIC FIXATION DEVICE

This is a continuation of application Ser. No. 08/396,624 filed on Mar. 1, 1995 now abandoned.

BACKGROUND OF THE INVENTION

1. Field of the Invention

The present invention relates, in general, to a device that allows complete repositioning of two members relative to one another and, more specifically, to an improved orthopedic external fixator including a mechanism that allows two bone elements or portions to be fixed relative to one another while allowing complete repositioning of the two bone elements or portions relative to one another.

2. Background Art

It is often necessary to realign, reposition and/or securely hold two elements relative to one another. For example, in the practice of medicine, bone fragments and the like must sometimes be aligned or realigned and repositioned to restore boney continuity and skeletal function, etc. At times this may be accomplished by sudden maneuver, usually followed by skeletal stabilization with cast, plate and screws, intramedullary devices, or external skeletal fixators.

A bone fragment can be moved, in general, from its original position as in a nonunion or malunion or from its intended position as in congenital deformities along six separate axes, a combination of three orthogonal translational axes (e.g., typical "X," "Y" and "Z" axes) and three orthogonal rotational axes (e.g., rotation about such typical "X," "Y" and "Z" axes).

Certain boney skeletal injuries or conditions are sometimes treated with an external device that is attached to the boney skeleton with threaded and/or smooth pins and/or threaded and/or smooth and/or beaded wires. Such constructs are commonly referred to as orthopedic external fixators or external skeletal fixators. External fixators may be utilized to treat acute fractures of the skeleton, soft tissue injuries, delayed union of the skeleton when bones are slow to heal, nonunion of the skeleton when bones have not healed, malunion whereby broken or fractured bones have healed in a malposition, congenital deformities whereby bones develop a malposition, and bone lengthening, widening, or twisting.

External fixators vary considerably in design and capabilities, and may include multiple or single bars or rods, and a plurality of clamps for adjustably securing the bars to pins or wires which are, in turn, joined to the boney skeleton. The pins or wires may extend completely through the boney skeleton extending out each side of the limb or may extend through the boney skeleton and out one side of the limb. Pins which extend completely through the boney skeleton and out both sides of the limb are commonly referred to as "transfixion pins." Pins which extend through the boney skeleton and out only one side of the limb are commonly referred to as "half pins." Such external fixators may be circumferential for encircling a patient's body member (e.g., a patient's femur), or may be unilateral for extending along one side of a patient's body member. More that one unilateral external fixator can be applied to the same length of the patient's body member. Materials for fixators also vary, including metals, alloys, plastics, composites, and ceramics. External fixators vary in their ability to accommodate different spatial relations between the pin and bar.

Prior art external fixators stabilize bone fragments by holding the fragments in a relatively fixed spatial relation. Some of the more completely adjustable external fixators allow the physician to reorient one fragment with respect to the other along all six axes in an acute motion, usually by loosening one or more clamps and effecting the corrective motion manually and retightening clamps to hold the fragments stably.

A circumferential external fixator system was disclosed by G. A. Ilizarov during the early 1950's. The Ilizarov system include at least two rings or "halos" that encircle a patient's body member (e.g., a patient's leg), connecting rods extending between the two rings, transfixion pins that extend through the patient's boney structure, and connectors for connecting the transfixion pins to the rings. Use of the Ilizarov system to deal with angulation, translation and rotation is disclosed in "Basic Ilizarov Techniques," *Techniques in Orthopaedics®*, Vol. 5, No. 4, December 1990, pages 55–59.

Mears, U.S. Pat. No. 4,620,533, issued Nov. 4, 1986, discloses a unilateral external fixator system including a plurality of fixation pins attached to at least one rigid bar through adjustable clamps having articulating balls which allow rotational adjustment of each pin or bar.

Stef, U.S. Pat. No. 5,209,750, issued May 11, 1993, discloses a unilateral external fixator system including an orthopedic brace for rigidly connecting groups of pins screwed into a long bone for the reduction of a fracture of the long bone. The brace includes a telescopic support made up of an elongated tube and an elongated rod slidable within the tube. A first plate is attached to the outer end of the tube and a second plate is attached to the outer end of the rod. Third and fourth plates are adjustably attached to the first and second plates, respectively, by way of threaded rods and ball-and-socket joints. Jaws are attached to each third and fourth plate to secure the pins to the brace.

Prior art orthopedic external fixators differ in their ability to move or adjust one bone fragment with respect to the other in a gradual fashion. Some allow gradual translation, others allow gradual rotation about two axes. The Ilizarov system can provide an external fixation device that could provide gradual correction along and about six axes; however such a device would require many parts and would be relatively complicated to build and use in a clinical situation.

Often orthopedic external fixators such as Ilizarov fixators must be modified later on after their initial application. Such modification may be necessary to convert from one correctional axis to another or to convert from an initial adjustment type of fixator to a weight bearing type of fixator, some of the correctional configurations not being stable enough for weight bearing.

More simplistic external fixators may accomplish a rotation of fragments about a center of rotation contained on the external fixator. This may or may not correspond to the center of rotation necessary to fully correct the deformity by angular correction alone. In no circumstances will a center of rotation confined to the external fixator create a virtual center of rotation remote to the external fixator as is frequently required in the treatment of these deformities. Some orthopedic external fixators utilize a simple hinge which cannot create a center of rotation remote to its mechanism. The Ilizarov system provides a circumferential encompassing type fixator that is more universal in that it permits the placement of the hinge axis around the bone, but does not allow rotation about an axis remote to its mechanism. A focal hinge made of an arc segment of gear or track with a following carriage can create a center of rotation remote to the mechanism but may not be applicable to certain situations where because of anatomy or preference the mechanism is to be applied to the concavity of a deformity, especially a severe deformity where there is no space to apply the long arc segment of gear or track necessary to fully correct the deformity.

Anderson, U.S. Pat. No. 2,391,537, issued Dec. 25, 1945, discloses an orthopedic external fixator for fracture reduction including a pair of hollow tubes telescopically joined together, a plurality of pins for transfixing bone elements, a first fixation unit slidably mounted on one of the tubes for connecting a pair of the transfixion pins to that tube, and a second fixation unit attached to the end of the other tube for connecting a pair of the transfixation pins to that tube. One of the tubes is telescopically mounted within the other tube. A threaded adjusting shaft is mounted within the tubes and can be manually rotated by way of a wrench head located at the outer end of one of the tubes. Rotation of the shaft causes a nut nonrotatably located within the tubes to move longitudinally along the shaft. Coil springs located within the tubes on either side of the nut transfer longitudinal movement of the nut to the tubes while permitting a certain desired yielding and eliminating any perfectly solid and hard contact. A geared mechanism allows for correction of rotational deformity, utilizing an arc segment of gear and a mating carriage with corresponding pinion.

A "Stewart platform" is a fully parallel mechanism used in flight and automotive simulators, robotic end-effectors, and other applications requiring spatial mechanisms with high structural stiffness; and includes a base platform, a top platform, and six variable limbs extending between the base and top platforms. See S. V. Sreenivasan et al., "Closed-Form Direct Displacement Analysis of a 6—6 Stewart Platform," *Mech. Mach. Theory*, Vol. 29, No. 6, pp. 855–864, 1994.

Nothing in the known prior art discloses or suggests the present invention. For example, nothing in the known prior art discloses a fixator that can be adjusted in six axes by changing strut lengths only, without requiring joints to be unclamped, etc. Further nothing in the known prior art discloses or suggests a mechanism including, in general, a first member or swash plate for attachment relative to a first element; a second member or swash plate for attachment relative to a second element; an adjustable effective length first strut having a first end movably attached to the first member and a second end movably attached to the second member; an adjustable effective length second strut having a first end movably attached to the first member and a second end movably attached to the second member; an adjustable effective length third strut having a first end movably attached to the first member and a second end movably attached to the second member; an adjustable effective length fourth strut having a first end movably attached to the first member and a second end movably attached to the second member; an adjustable effective length fifth strut having a first end movably attached to the first member and a second end movably attached to the second member; and an adjustable effective length sixth strut having a first end movably attached to the first member and a second end movably attached to the second member, with the first ends of the first and second struts joined relative to one another so that movement of the first end of one of the first and second struts will cause a corresponding movement of the first end of the other strut, with the first ends of the third and fourth struts joined relative to one another so that movement of the first end of one of the third and fourth struts will cause a corresponding movement of the first end of the other strut, with the first ends of the fifth and sixth struts joined relative to one another so that movement of the first end of one of the fifth and sixth struts will cause a corresponding movement of the first end of the other strut, with the second ends of the first and sixth struts joined relative to one another so that movement of the second end of one of the first and sixth struts will cause a corresponding movement of the second end of the other strut, with the second ends of the second and third struts joined relative to one another so that movement of the second end of one of the second and third struts will cause a corresponding movement of the second end of the other strut, with the second ends of the fourth and fifth struts joined relative to one another so that movement of the second end of one of the fourth and fifth struts will cause a corresponding movement of the second end of the other strut.

SUMMARY OF THE INVENTION

The present invention provides a novel device that allows two elements to be positioned relative to one another while allowing complete repositioning of the two elements relative to one another. A basic concept of the present invention is to provide an eight member device that allows two elements to be positioned or fixed relative to one another while allowing complete repositioning of the two elements relative to one another.

The device of the present invention includes, in general, a first member or swash plate for attachment relative to a first element; a second member or swash plate for attachment relative to a second element; an adjustable effective length first strut having a first end movably attached to the first member and a second end movably attached to the second member; an adjustable effective length second strut having a first end movably attached to the first member and a second end movably attached to the second member; an adjustable effective length third strut having a first end movably attached to the first member and a second end movably attached to the second member; an adjustable effective length fourth strut having a first end movably attached to the first member and a second end movably attached to the second member; an adjustable effective length fifth strut having a first end movably attached to the first member and a second end movably attached to the second member; and an adjustable effective length sixth strut having a first end movably attached to the first member and a second end movably attached to the second member. The first ends of the first and second struts are joined relative to one another so that movement of the first end of one of the first and second struts will cause a corresponding movement of the first end of the other strut. The first ends of the third and fourth struts are joined relative to one another so that movement of the first end of one of the third and fourth struts will cause a corresponding movement of the first end of the other strut. The first ends of the fifth and sixth struts are joined relative to one another so that movement of the first end of one of the fifth and sixth struts will cause a corresponding movement of the first end of the other strut. The second ends of the first and sixth struts are joined relative to one another so that movement of the second end of one of the first and sixth struts will cause a corresponding movement of the second end of the other strut. The second ends of the second and third struts are joined relative to one another so that movement of the second end of one of the second and third struts will cause a corresponding movement of the second end of the other strut. The second ends of the fourth and fifth struts are joined relative to one another so that movement of the second end of one of the fourth and fifth struts will cause a corresponding movement of the second end of the other strut.

One object of the present invention is to provide a device that allows complete repositioning of two or more elements such as two or more bone fragments.

Another object of the present invention is to provide a device that allows sudden repositioning of two or more elements to be accomplished predictably and which may be left in place for additional time or may be replaced by other means of stabilization.

Another object of the present invention is to provide a device that allows gradual repositioning of two or more elements over an extended period of time either in an incremental fashion with discreet adjustments or continuous motion if motorized, etc.

Another object of the present invention is to provide a device that allows a slow controlled reposition of two or more elements.

Another object of the present invention is to provide a device that is capable of correcting all six degrees of freedom and at no time is unstable to move grossly unless the gross motion locks are loosened.

Another object of the present invention is to provide a device that allows relative repositioning of two or more elements by changing the effective lengths of six similar struts, either gradually or suddenly.

Another object of the present invention is to provide a device that can move one fragment with respect to the other in six orthogonal degrees of freedom, a combination of three orthogonal translational axes (e.g., typical "X," "Y" and "Z" axes) and three orthogonal rotational axes (e.g., rotation about such typical "X," "Y" and "Z" axes), limited in extent of relative repositioning only by the physical constraints of the device.

Another object of the present invention is to provide a device that is relatively compact, to some extent telescoping upon itself.

Another object of the present invention is to provide a device that is universal in that it can be used for any situation requiring relative motion between elements including compression (shortening), distraction (lengthening), translation, angulation, or rotation and any combination of such movements.

Another object of the present invention is to provide a device that can create a center of rotation of the elements to be fixed relative to one another that may be remote to the spatial frame itself, but may also allow rotation within or close to the frame confines.

Another object of the present invention is to provide a device that allows coarse and/or fine adjustment of the relative position of two or more elements.

Another object of the present invention is to provide a mechanism for producing a prescribed relative change in position between two bone fragments in conjunction with external fixation of the bone fragments for correction of angular and translational displacements of acutely fractured fragments, correction of angular and translational deformities in nonunion and malunion, etc.

Another object of the present invention is to provide a device having a universal repositioning character.

Another object of the present invention is to provide a device having an overall simplicity of construction and use unlike other external fixators.

Another object of the present invention is to provide a device having six similar struts which can be adjusted in length and attached at either end by passive, clamping or non-clamping joint connections to two end members.

Another object of the present invention is to provide a device that is self locking and not prone to spontaneous slippage due to the inherent stability of strut adjustment mechanisms to resist rotation when loaded in tension or compression. The strut adjustment mechanism could include turnbuckles, gear and rack, screw and nut, or hydraulic cylinder, etc., and may include means of coarse and fine adjustment thereby allowing rapid approximation and subsequent precise adjustments.

Another object of the present invention is to provide a device that utilizes struts that are purposely angled with respect to the long axis. This angulation provides mechanical characteristic which allows the present invention to correct all six degrees of freedom.

Another object of the present invention is to provide a device that can be adjusted to move elements such as bone fragments from one relative position to another without losing control of the elements while making all degrees of freedom always available without having to reposition element fixation pins or wires and without having to reposition the point of attachment of the struts.

Another object of the present invention is to provide a device that can be completely repositioned by changing the effective lengths of the struts by adjusting the effective length of one or more struts.

Another object of the present invention is to provide a device that is especially designed for, but not limited to, securely holding bone fragments, repositioning bone fragments, and reproducing joint motion.

Another object of the present invention is to provide a device that may be used to reposition any two bodies relative to each other.

Another object of the present invention is to provide a device that can also be used as a telescope frame with the primary mirror attached to one swash plate and the secondary mirror attached to the opposite swash plate with the six struts acting not only as a stabilizing but also provide means for aligning and positioning the mirrors/lenses with respect to each other.

Another object of the present invention is to provide a device that can be used in the laboratory for positioning components, and in construction to reposition two members.

Another object of the present invention is to provide a device that can be considered both frame and mechanism. To the extent that each combination of lengths for the six struts yields a stable construct, the present invention provides a stabilizing device for bone fragments and functions as a skeletal external fixation device. To the extent that changing the effective lengths of one or more of the struts results in relative motion between the swash plates, the present invention provides a mechanism for moving bone fragments.

Another object of the present invention is to provide a device that can be used to reestablish skeletal joint motion after injury or disease by being attached to either side of a skeletal joint to reproduce not only hinge type motion most like the elbow or ankle joints, but more complex motions such as those with changing instant centers of rotation, or even spherical motion like the hip by allowing one bone fragment to be moved along six independent axes with respect to another bone fragment.

Another object of the present invention is to provide a device that does not have to be mounted exactly along a particular axis at the time of initial attachment or surgery.

Another object of the present invention is to provide a device in which the orientation of the device with respect to the skeletal joint can be determined after the device is applied and the relative lengthening or shortening of the six struts necessary to provide the preferred motion can then be determined.

Another object of the present invention is to provide a device having ball joints composed of two hemispheres, or a hyperhemisphere in conjunction with a hypohemisphere.

Another object of the present invention is to provide a device having three or more bodies contained with a spherical socket.

Another object of the present invention is to provide a device that operates as a true parallel and simultaneous manipulator.

Another object of the present invention is to provide a device in which the only adjustments necessary for correcting one or six orthogonal deformities is to simply change strut lengths, regardless of whether a translation or angulation or combination of up to three orthogonal rotations and three orthogonal translations is desired.

Another object of the present invention is to provide a device which is not limited to "serial" mechanisms or steps to accomplish a six axis correction.

Another object of the present invention is to provide a device in which all the struts are free to rotate at each end.

Another object of the present invention is to provide a device which allows six axes correction without limiting the correction to a sudden correction in which a number of joints or all of the joints are loosened, the frame moved, and the joints then retightened.

Another object of the present invention is to provide a device in which all coupling joints (strut to end plate) are not clamped while the device, even though not clamped, provides stability by virtue of its geometry with angled struts.

Another object of the present invention is to provide a device that uses passive unclamped joints to couple six struts to two end plates or bodies.

Another object of the present invention is to provide a device which can correct a six axis deformity in a controlled fashion.

Another object of the present invention is to provide a device having six angled struts with the joints at the end of each strut left free to rotate and with the geometry of the six strut fixator providing a stable device.

Another object of the present invention is to provide a device that allows slow controlled repositioning of two or more bone fragments only during lengthening along the long axis and also during correction of angular deformity.

Another object of the present invention is to provide a device that allows gradual or sudden adjustment of the effective length thereof.

Another object of the present invention is to provide a device that allows biologically compatible relative velocities between bone fragments on the order of one millimeter per day.

Another object of the present invention is to provide a device that can predictably and reproducibly cause small displacements between bone fragments.

Another object of the present invention is to provide a device that allows coordinate transformation based on mathematical computation of only three points on one end plate and resulting changes in length of six struts spanning only six points.

Another object of the present invention is to provide a device that functions, kinematically speaking, generally as a parallel manipulator in that the basic device is capable of accomplishing a simultaneous six degree of freedom motion of bone fragments relative to one another.

Another object of the present invention is to provide a device including two base members jointed by a plurality of adjustable effective length struts with the ends of each strut coupled to a base member by a shared joint (i.e., a joint shared with the end of another strut) or a non-shared joint.

Another object of the present invention is to provide an external fixator that allows a surgeon to reposition bone fragments without having to first loosen a plurality of joints, then reposition the bone fragments, and then retightened the plurality of joints.

Another object of the present invention is to provide a device having two base members and at least six struts joining the two base members together with shared vertices with six shared vertices or coupling of struts to the base members for repositioning objects including bone fragments.

Another object of the present invention is to provide a device having a ball-and-socket joint with four degrees of freedom (i.e., in addition to rotation about three orthogonal axes as typically accomplished by conventional ball-and-socket joints, the ball-and-socket joint of the present invention includes hemispheres which are additionally free to rotate about an axis perpendicular to the face of each hemisphere passing through the center of the hemispheres).

Another object of the present invention is to provide a device having struts that are attached to end or base members by couplings which permits rotation (the exact number of rotations being determined by the type of coupling), that maintains its position until one or more strut lengths are adjusted, that permits a gradual predictable corrective motion, that has stability provided by purposely angling the struts to create a "triangle" that prevents motion along the orthogonal axes, and not by creating a clamping force at the couplings.

Another object of the present invention is to provide a device that does not require the joints between the struts and base members to be clamped to prevent unwanted motion or to prevent motion after reduction.

Another object of the present invention is to provide a device that maximizes the amount of space on the end plates for attachment of pin clamps and eases space restrictions.

Another object of the present invention is to provide a device that can be used in small sizes in situations where space is at a premium, for example, in external fixation of children's bones.

Another object of the present invention is to provide external fixation, telescopes, laboratory or construction jacks.

Another object of the present invention is to provide a new use for a Stewart platform. More specifically, another object of the present invention is to use a Stewart platform in orthopedics to secure first and second bone elements relative to one another.

BRIEF DESCRIPTION OF THE DRAWINGS

FIG. 8 is a front elevational view of portions of an adjustable effective length strut of the external fixator of FIG. 1.

FIG. 9 is a sectional view substantially as taken on line 9—9 of FIG. 8.

FIG. 10 is a sectional view of pans of a modified embodiment of a connector means of the present invention.

FIG. 11 is a perspective view of a modified embodiment of a connector of the present invention.

FIG. 12 is an exploded perspective view of FIG. 11.

FIG. 25 is an exploded view of an alternate arrangement of a base member and associated structure for use with the embodiment of FIGS. 1-10.

FIG. 26 is an exploded view of an alternate arrangement of a base member and associated structure for use with the embodiment of FIGS. 19 and 20.

FIG. 27 is a sectional view similar to FIG. 4 but showing modified embodiments of the adjustable effective length struts and connector means of the present invention.

DESCRIPTION OF THE PREFERRED EMBODIMENTS

Figure 1:
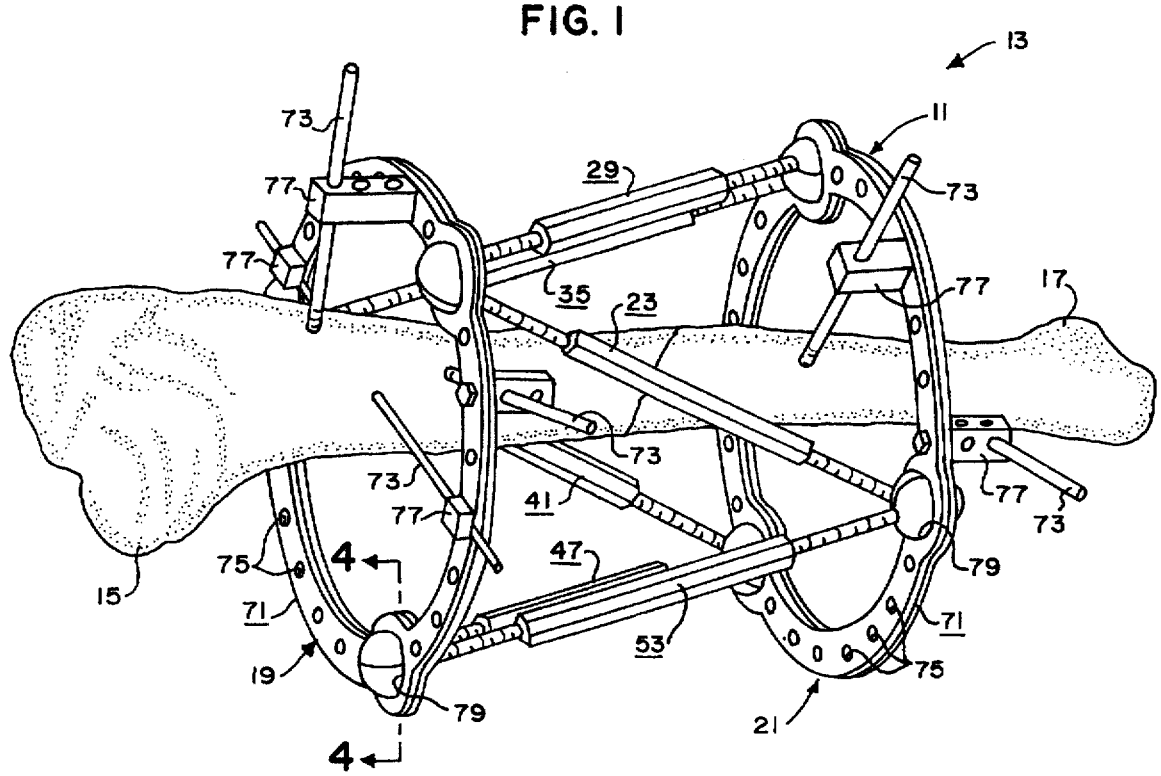
FIG. 1 is a perspective view of a first preferred embodiment of the external fixator of the present invention shown in combination with other elements of an orthopedic external fixator and a fractured tibia.
Figure 2:
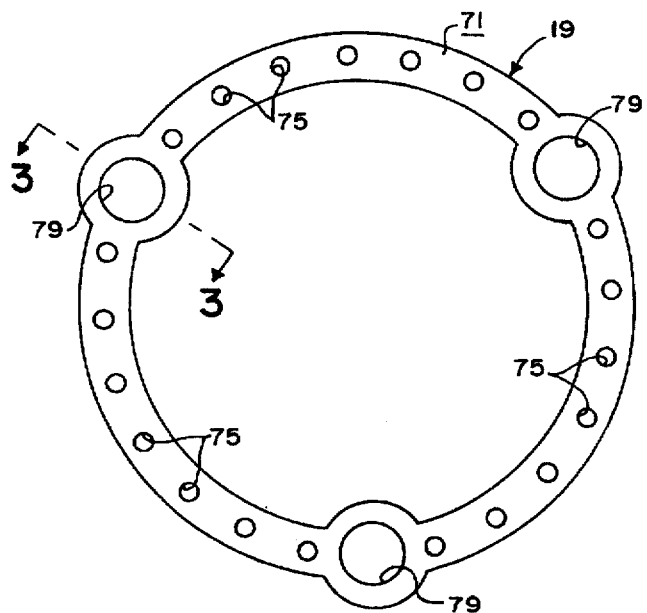
FIG. 2 is an end elevational view of one end plate of the external fixator of FIG. 1.
Figure 3:
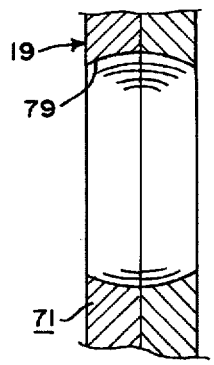
FIG. 3 is a sectional view substantially as taken on line 3—3 of FIG. 2 on an enlarged scale with portions thereof omitted for clarity.
Figure 4:
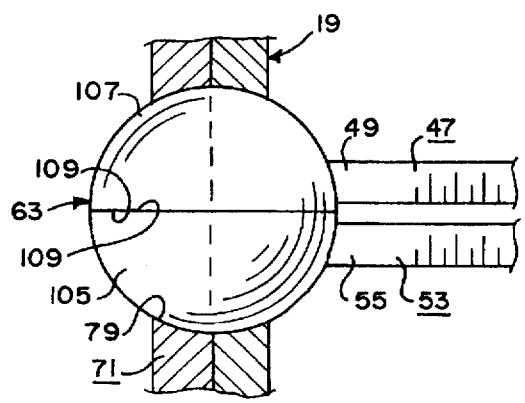
FIG. 4 is a sectional view substantially as taken on line 4—4 of FIG. 1 on an enlarged scale and with portions omitted and broken away for clarity.
Figure 5:
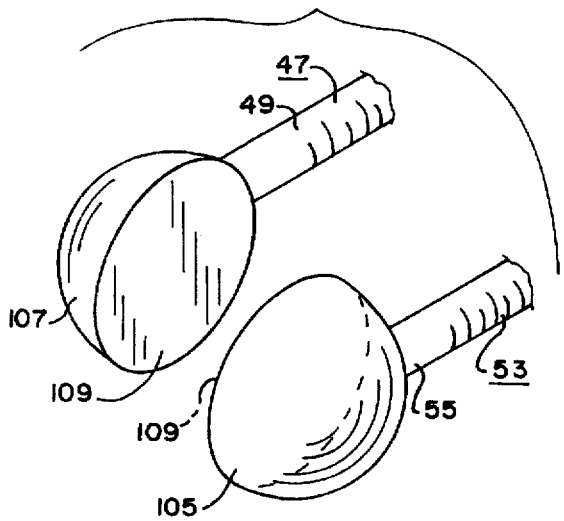
FIG. 5 is an exploded perspective view of parts of one of the connector means of the external fixator of FIG. 1.
Figure 6:
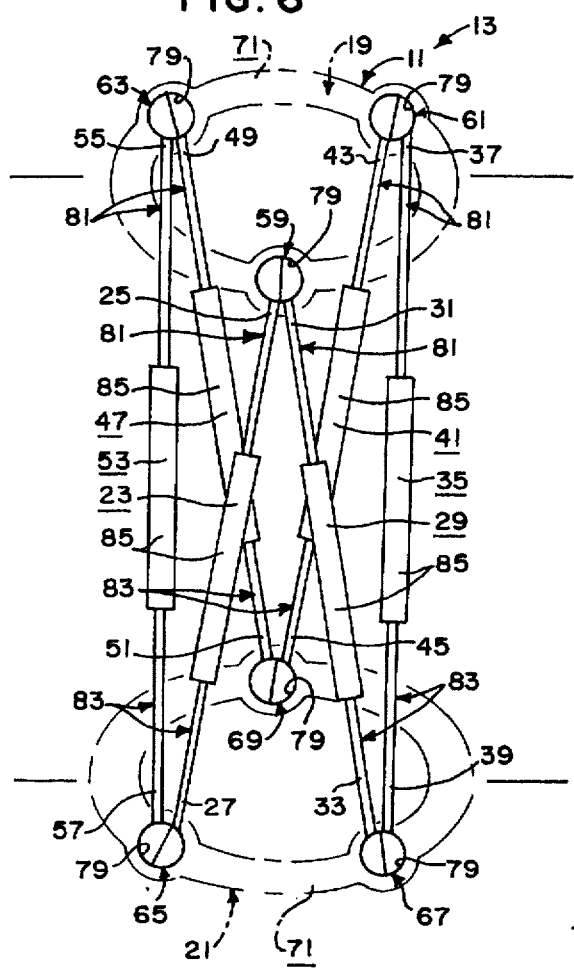
FIG. 6 is a diagrammatic view of the external fixator of FIG. 1 shown in a first spatial arrangement.
Figure 7:
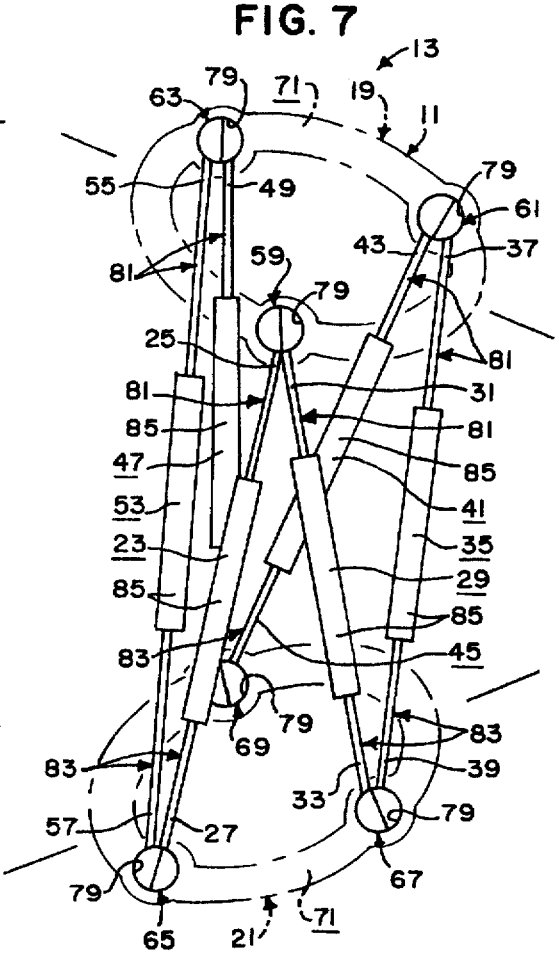
FIG. 7 is a diagrammatic view of the spatial frame of FIG. 1 in a second spatial arrangement.

A first preferred embodiment of the present invention is shown in FIGS. 1-9, and identified by the numeral 11. The external fixator 11 is part of a circumferential-type orthopedic external fixator 13 for securing a first bone element 15 relative to a second bone element 17.

The external fixator 11 includes a first base member 19 for attachment to the first bone element 15; a second base member 21 for attachment to the second bone element 17; an adjustable effective length first strut 23 having a first end 25 and a second end 27; an adjustable effective length second strut 29 having a first end 31 and a second end 33; an adjustable effective length third strut 35 having a first end 37 and a second end 39; an adjustable effective length fourth strut 41 having a first end 43 and a second end 45; an adjustable effective length fifth strut 47 having a first end 49 and a second end 51; an adjustable effective length sixth strut 53 having a first end 55 and a second end 57; first connector means 59 for rotatably attaching the first ends 25, 31 of the first and second struts 23, 29 relative to one another and relative to the first base member 19; second connector means 61 for rotatably attaching the first ends 37, 43 of the third and fourth struts 35, 41 relative to one another and relative to the first base member 19; third connector means 63 for rotatably attaching the first ends 49, 55 of the fifth and sixth struts 47, 53 relative to one another and relative to the first base member 19; fourth connector means 65 for rotatably attaching the second ends 27, 57 of the first and sixth struts 23, 53 relative to one another and relative to the second base member 21; fifth connector means 67 for rotatably attaching the second ends 33, 39 of the second and third struts 29, 35 relative to one another and relative to the second base member 21; and sixth connector means 69 for rotatably attaching the second ends 45, 51 of the fourth and fifth struts 41, 47 relative to one another and relative to the second base member 21. When used herein, the phrase "rotatably attaching" when describing the attachment between two or more parts or elements means that the referenced parts or elements are attached to one another in such a manner that allows rotation therebetween.

The first and second base members 19, 21 may be constructed in various manners, out of various materials, and in various shapes and sizes. Thus, for example, each base member 19, 21 may consist of a one-piece or multi-piece Ilizarov-type halo or ring 71 for encircling a patient's limb, etc. and for being secured to one of the bone elements 15, 17 or the like by way of transfixation screws, wires or pins 73, etc., as will now be apparent to those skilled in the art. Each ring 71 preferably has a plurality of spaced apertures 75 therethrough for allowing the transfixation screws, wires or pins 73, etc., to be secured thereto with typical fixator clamps 77 or the like as will now be apparent to those skilled in the art. The spaced apertures 75 may also be used to join the various connector means 59, 61, 63, 65, 67, 69 to the respective ring 71. However, with respect to the preferred embodiment shown in FIGS. 1-7, each ring 71 preferably differs from a typical Ilizarov-type ring by having a plurality of partially spherical cavities 79 for reasons which will hereinafter become apparent. The partially spherical cavities 79 may be formed integrally with the rings 71 as shown clearly in FIGS. 2-4. On the other hand, each partially spherical cavity 79 may be formed in a plate member 80 that can be bolted or otherwise fixedly attached to one of the rings 71 as clearly shown in FIG. 25 and as will now be apparent to those skilled in the art. Additional, each partially spherical cavity 79 may be partially formed in the rings 71 and partially formed in separate plate members which coact with one another to define the partially spherical cavities 79, etc.

Each of the struts 23, 29, 35, 41, 47, 53 are preferably similar in construction to one another. The construction and operation of each strut 23, 29, 35, 41, 47, 53 may vary and may be designed to provide coarse and/or fine adjustment of the effective length thereof. When used herein, the phrase "effective length" when describing the length of one or more struts 23, 29, 35, 41, 47, 53 means the distance between the center of rotation of two associated connector means 59, 61, 63, 65, 67, 69. The embodiment of each strut 23, 29, 35, 41, 47, 53 shown generally in FIGS. 1–9 includes a first component 81, a second component 83, and coupling means 85 for adjustably coupling the first and second components 81, 83 to one another. Each first component 81 preferably includes an elongated rod 87 having a threaded end 89. Each second component 83 preferably includes an elongated rod 91 having a threaded end 93. Each coupling means 85 preferably has a first threaded portion 95 for coacting with the threaded end 89 of the rod 87 of the first components 81 and a second threaded portion 97 for coacting with the threaded end 93 of the rod 91 of the second component 83. The threaded end 89, threaded end 93, first threaded portion 95, and second threaded portion 97 are preferably designed so that rotation of the coupling means 85 about its longitudinal axis will cause the first and second components 81, 83 to move in opposite directions. Thus, for example, the threaded end 89 of the first component 81 and the first threaded portion 95 of the coupling means 85 may have coacting right-hand threads while the threaded end 93 of the second component 83 and the second threaded portion 97 of the coupling means 85 may have coacting left-hand threads, or vice versa, so that rotating the coupling means 85 about its longitudinal axis will cause the associated parts to act like or as a turnbuckle to either extend or retract the first and second components 81, 83 relative to one another and the coupling means 85 and thereby adjust or vary the overall length of each strut 23, 29, 35, 41, 47, 53 as will now be apparent to those skilled in the art. Also, while the threaded end 89 of the rod 87 and the threaded end 93 of the rod 91 are shown in the drawings as male threads and while the threaded portions 95, 97 of the coupling means 85 are shown in the drawings as female threads, an opposite construction can be used (i.e., having female threads on the threaded end 89 of the rod 87 and the threaded end 93 of the rod 91, and male threads on the threaded portions 95, 97 of the coupling means 85).

It should be understood that the effective length of each strut 23, 29, 35, 41, 47, 53 can be adjusted in various other manners and by various other means. For example, each strut 23, 29, 35, 41, 47, 53 could include a hydraulic or pneumatic piston, electric motor and gear trains, etc., and various controls for allowing the effective length of each strut 23, 29, 35, 41, 47, 53 to be easily and accurately controlled. Further, each strut 23, 29, 35, 41, 47, 53 could consist of a one-piece, integral rod with threaded ends and each connector means 59, 61, 63, 65, 67, 69 could have a threaded aperture for coacting therewith as more fully described hereinbelow with reference to the embodiment of FIG. 27.

The frame 11 may include indicia or gauge means 99 for providing an indication or relative measurement of the effective length of each strut 23, 29, 35, 41, 47, 53. For example, as shown in FIGS. 8 and 9, the coupling means 85 of each strut 23, 29, 35, 41, 47, 53 may have one or more elongated slots 101 which allows portions of the distal end of each component 81, 83 of each strut 23, 29, 35, 41, 47, 53 to be viewed therethrough, and a plurality of spaced apart indicia marks 103 or the like along the effective length of the slots 101 forming a graduated scale so that an accurate indication of the effective length of each strut 23, 29, 35, 41, 47, 53 can be easily and quickly determined by merely noting the position of a certain portion of each component 81, 83 relative to the indicia marks 103. Thus, for example, the indicia marks 103 may be graduated so that the alignment of the distal end 104 of each elongated rod 87, 91 with a certain indicia mark 103 as clearly shown in FIG. 8 will provide an indication or relative measurement of the overall length of each strut 23, 29, 35, 41, 47, 53 as will now be apparent to those skilled in the art.

In the embodiments shown in FIGS. 1–7 and 10, each of the connector means 59, 61, 63, 65, 67, 69 consists of a split-ball connector including a first partially spherical member 105 attached to one of the ends 25, 27, 31, 33, 37, 39, 43, 45, 49, 51, 55, 57 of one of the struts 23, 29, 35, 41, 47, 53, and a second partially spherical member 107 attached to one of the ends 25, 27, 31, 33, 37, 39, 43, 45, 49, 51, 55, 57 of another of the struts 23, 29, 35, 41, 47, 53. Each of the partially spherical members 105, 107 of the connector means 59, 61, 63, 65, 67, 69 preferably has a planar face portion 109. Each of the partially spherical cavities 79 in the ring 71 of each base member 19, 21 is preferably sized and designed for rotatably entrapping a respective pair of the partially spherical members 105, 107 of the connector means 59, 61, 63, 65, 67, 69 with the planar face portions 109 thereof held movably against one another (see, for example, FIG. 4). While not necessary, each connector means 59, 61, 63, 65, 67, 69 may include pivot means such as a pivot rod 111 extending through the center of each planar face portion 109 of a coacting pair of partially spherical members 105, 107 for pivotally joining that pair of partially spherical members 105, 107 together as clearly shown in FIG. 10.

The split-ball connectors of FIGS. 1–7 and 10 have certain advantages. They save space since only three split-ball joints are necessary per swash plate or base member 19, 21 versus six separate joints if spherical ball joints on the end of each strut 23, 29, 35, 41, 47, 53. Also, if spherical ball joints are used on the end of each strut 23, 29, 35, 41, 47, 53, when adjusting the effective length of any strut 23, 29, 35, 41, 47, 53 using the turnbuckle structure shown in FIGS. 1–9, there would be a tendency for the threaded half shafts and ball to rotate, preventing predictable adjustment in strut length. However, the split-ball connectors of FIGS. 1–7 and 10, containing hemispheres attached to adjacent struts, would prevent either hemisphere from rotating independently about its strut axis, but would allow the combined split ball joint to rotate about three axes as a unit. Therefore, when adjusting the effective length of any individual strut 23, 29, 35, 41, 47, 53 by rotating the coupling means 85, rotation of the corresponding rod 87, 91 is blocked by the coaction of the split-ball connectors. It would be necessary to block rotation of the corresponding rod 87, 91 whenever a coupling means 85 is rotated if using spherical ball joints on the end of each strut 23, 29, 35, 41, 47, 53 as will now be apparent to those skilled in the art.

In the embodiment shown in FIGS. 11 and 12, each of the connector means 59, 61, 63, 65, 67, 69 consists of a split U-joint connector or the like. While only the connector means 65 is shown in FIGS. 11 and 12, the other connector means 59, 61, 63, 67, 69 are preferably similar or identical in construction thereto. The split U-joint connector as shown in FIGS. 11 and 12 includes a first member 113, a shaft member 115 for attaching the first member 113 to a respective one of the first and second base members 19, 21, a second member 117, a pivot member 119 for pivotally attaching the second member 117 to the first member 113 with the longitudinal axis 121 of the pivot member 119 extending transverse to the longitudinal axis 123 of the shaft member 115, and a pivot member 125 for pivotally attaching one of the ends 25, 27, 31, 33, 37, 39, 43, 45, 49, 51, 55, 57 of one of the struts 23, 29, 35, 41, 47, 53 and one of the ends 25, 27, 31, 33, 37, 39, 43, 45, 49, 51, 55, 57 of another of the struts 23, 29, 35, 41, 47, 53 to the second member 117 (shown pivotally attaching the end 27 of the strut 23 and the end 57 of the strut 53 to the second member 117) with the longitudinal axis 127 of the pivot member 125 extending transverse to the longitudinal axis 121 of the pivot member 119. The ends 25, 27, 31, 33, 37, 39, 43, 45, 49, 51, 55, 57 of the struts 23, 29, 35, 41, 47, 53 may include enlarged heads 129 through which the pivot member 125 extend as indicated in FIGS. 11 and 12. The shaft member 115 may be bolted or press-fitted or otherwise securely attached to the first member 113 or may be formed as an integral, one-piece unit with the first member 113, or may be rotatably secured to the respective base member 19, 21 by a typical retainer clip or the like as will now be apparent to those skilled in the art for pivotally attaching the first member 113 to a respective one of the first and second base members 19, 21. The pivot member 119 may be press-fitted or otherwise securely attached to the second member 117 or may be formed as an integral, one-piece unit with the second member 117, and may be rotatably secured to the first member 113 by a typical retainer clip or the like as will now be apparent to those skilled in the art. The pivot member 125 may be press-fitted or otherwise securely attached to one of the coacting members (i.e., the second member 117 or one of the enlarged heads 129) or may be formed as an integral, one-piece unit with one of the coacting members (i.e., the second member 117 or one of the enlarged heads 129), or may be rotatably secured relative to each coacting member (i.e., to the second member 117 and both of the enlarged heads 129) by typical retainer clips or the like as will now be apparent to those skilled in the art.

Figure 13:
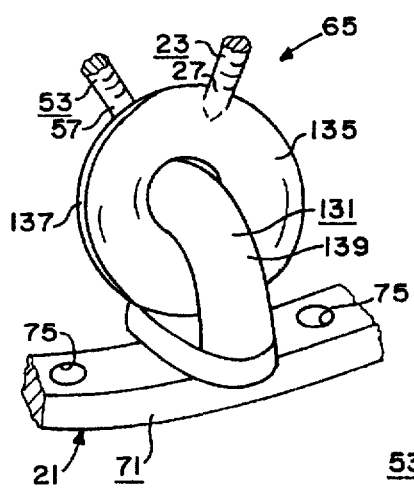
FIG. 13 is a perspective view of another modified embodiment of a connector means of the present invention.
Figure 14:
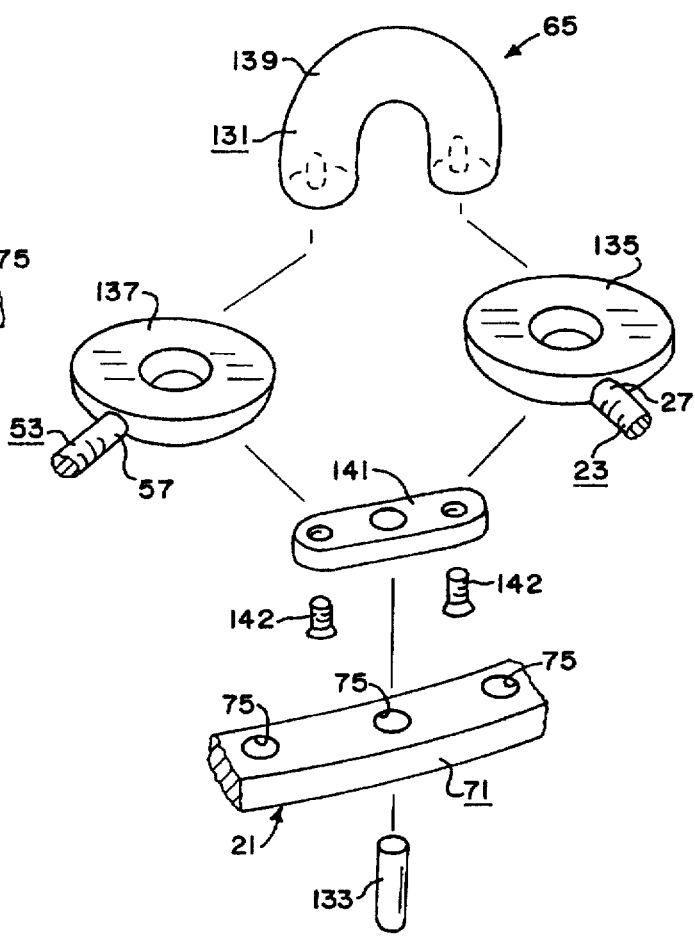
FIG. 14 is an exploded perspective view of FIG. 13.

In the embodiment shown in FIGS. 13 and 14, each of the connector means 59, 61, 63, 65, 67, 69 consists of a split chain link connector or the like. While only the connector means 65 is shown in FIGS. 13 and 14, the other connector means 59, 61, 63, 67, 69 are preferably similar or identical in construction thereto. The split chain link connector as shown in FIGS. 13 and 14 includes a first ring member 131, a shaft member 133 attaching the first ring member 131 to a respective one of the first and second base members 19, 21, a second ring member 135 attached to one of the ends 25, 27, 31, 33, 37, 39, 43, 45, 49, 51, 55, 57 of one of the struts 23, 29, 35, 41, 47, 53 (shown attached to the end 27 of the strut 23) and pivotally attached to the first ring member 131, and a third ring member 137 attached to one of the ends 25, 27, 31, 33, 37, 39, 43, 45, 49, 51, 55, 57 of another of the struts 23, 29, 35, 41, 47, 53 (shown attached to the end 57 of the strut 53) and pivotally attached to the first and second ring members 131, 135. Each first ring member 131 is preferably formed by a U-shaped member 139 for extending through the second and third ring members 135, 137, and a bridge member 141 for closing the U-shaped member 139 after the U-shaped member 139 is passed through the central hole in the second and third ring members 135, 137. The bridge member 141 may be removably attached to the U-shaped member 139 by screws 142 or the like (see FIG. 14). The shaft member 133 may be bolted, press-fitted or otherwise securely attached to the bridge member 141 or may be formed as an integral, one-piece unit with the bridge member 141, or may be rotatably secured to both the bridge member 141 and the respective base member 19, 21 by typical retainer clips or the like as will now be apparent to those skilled in the art to pivotally attach the first ring member 131 to a respective one of the first and second base members 19, 21. The method of attaching the second and third ring members 135, 137 to the respective ends 25, 27, 31, 33, 37, 39, 43, 45, 49, 51, 55, 57 of the struts 23, 29, 35, 41, 47, 53 may vary as will now be apparent to those skilled in the art. Thus, for example, each ring member 135, 137 may be integrally formed as a one-piece unit with a respective end 25, 27, 31, 33, 37, 39, 43, 45, 49, 51, 55, 57 of a respective strut 23, 29, 35, 41, 47, 53 as will now be apparent to those skilled in the art.

Figure 15:
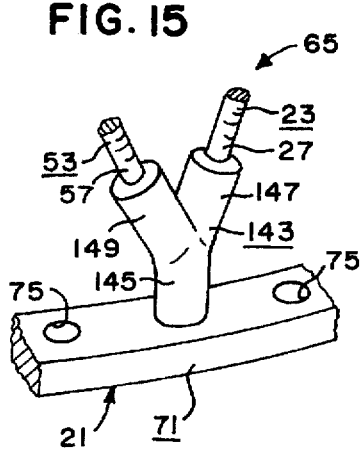
FIG. 15 is a perspective view of yet another modified embodiment of a connector means of the present invention.
Figure 16:
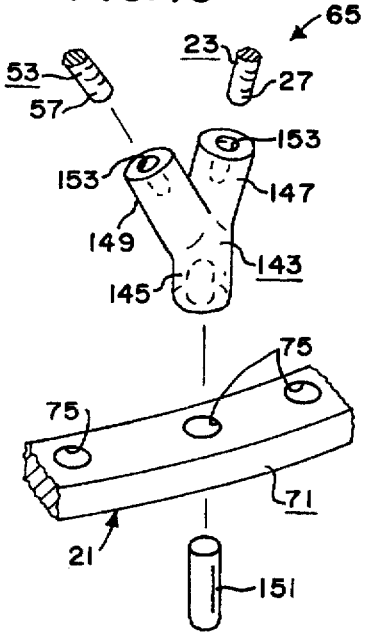
FIG. 16 is an exploded perspective view of FIG. 15.

In the embodiment shown in FIGS. 15 and 16, each of the connector means 59, 61, 63, 65, 67, 69 consists of a flexible or elastic connector. While only the connector means 65 is shown in FIGS. 15 and 16, the other connector means 59, 61, 63, 67, 69 are preferably similar or identical in construction thereto. The flexible or elastic connector as shown in FIGS. 15 and 16 includes a flexible or elastic Y-shaped body member 143 constructed out of a flexible or elastic rubber or the like with a trunk portion 145 for attachment to a respective one of the first and second base members 19, 21, a first arm 147 for attachment to one of the ends 25, 27, 31, 33, 37, 39, 43, 45, 49, 51, 55, 57 of one of the struts 23, 29, 35, 41, 47, 53 (shown attached to the end 27 of the strut 23), and a second arm 149 for attachment to one of the ends 25, 27, 31, 33, 37, 39, 43, 45, 49, 51, 55, 57 of another one of the struts 23, 29, 35, 41, 47, 53 (shown attached to the end 57 of the strut 53). While the trunk portion 145 may be fixedly attached to a respective one of the first and second base members 19, 21 due to the flexibility or elasticity thereof, a shaft member 151 may be provided for connecting the trunk portion 145 to a respective one of the first and second base members 19, 21. The shaft member 151 may be bolted or press-fitted or otherwise securely attached to the trunk portion 145 or may be formed as an integral, one-piece unit with the trunk portion 145, or may be rotatably secured to the respective base member 19, 21 by a typical retainer clip or the like as will now be apparent to those skilled in the art to pivotally connect the trunk portion 145 to a respective one of the first and second base members 19, 21. The method of attaching the first and second arms 147, 149 to the respective ends 25, 27, 31, 33, 37, 39, 43, 45, 49, 51, 55, 57 of the struts 23, 29, 35, 41, 47, 53 may vary as will now be apparent to those skilled in the art. Thus, for example, the respective ends 25, 27, 31, 33, 37, 39, 43, 45, 49, 51, 55, 57 of the struts 23, 29, 35, 41, 47, 53 may be externally threaded and each arm portion 147, 149 may have a threaded aperture 153 for threadably receiving the respective ends 25, 27, 31, 33, 37, 39, 43, 45, 49, 51, 55, 57 of the struts 23, 29, 35, 41, 47, 53. The threaded aperture 153 may be formed in a tubular metal insert in each arm portion 147, 149 as will now be apparent to those skilled in the art.

Figure 17:
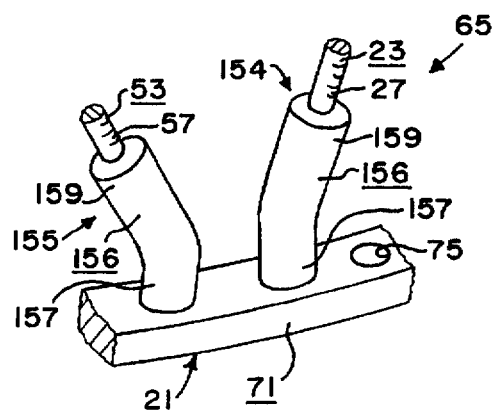
FIG. 17 is a perspective view of yet another modified embodiment of a connector means of the present invention.
Figure 18:
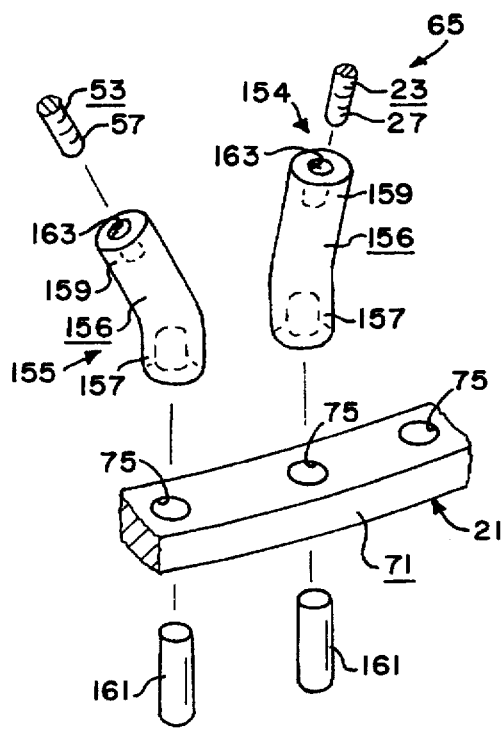
FIG. 18 is an exploded perspective view of FIG. 17.

In the embodiment shown in FIGS. 17 and 18, each of the connector means 59, 61, 63, 65, 67, 69 consists of a flexible or elastic connector. While only the connector means 65 is shown in FIGS. 17 and 18, the other connector means 59, 61, 63, 67, 69 are preferably similar or identical in construction thereto. The flexible or elastic connector as shown in FIGS. 17 and 18 includes a first body means 154 attached to a respective one of the first and second base members 19, 21 and to one of the ends 25, 27, 31, 33, 37, 39, 43, 45, 49, 51, 55, 57 of one of the struts 23, 29, 35, 41, 47, 53, and a second body means 155 attached to the respective one of the first and second base members 19, 21 adjacent and independently of the first body means 154 and to one of the ends 25, 27, 31, 33, 37, 39, 43, 45, 49, 51, 55, 57 of one of the struts 23, 29, 35, 41, 47, 53. Each body means 154, 155 preferably includes a flexible or elastic body member 156 constructed out of a flexible or elastic rubber or the like with a first end portion 157 for attachment to a respective one of the first and second base members 19, 21, and a second end portion 159 for attachment to one of the ends 25, 27, 31, 33, 37, 39, 43, 45, 49, 51, 55, 57 of one of the struts 23, 29, 35, 41, 47, 53 (FIGS. 17 and 18 show the first body means 154 attached to the end 27 of the strut 23 and the second body means 155 attached to the end 57 of the strut 53). While the first end portion 157 may be fixedly attached to a respective one of the first and second base members 19, 21 due to the flexibility or elasticity thereof, a shaft member 161 may be provided for connecting the first end portion 157 to a respective one of the first and second base members 19, 21. The shaft member 161 may be bolted or press-fitted or otherwise securely attached to the first end portion 157 or may be formed as an integral, one-piece unit with the first end portion 157, or may be rotatably secured to the respective base member 19, 21 by a typical retainer clip or the like as will now be apparent to those skilled in the art for pivotally connecting the first end portion 157 to a respective one of the first and second base members 19, 21. The method of attaching the respective ends 25, 27, 31, 33, 37, 39, 43, 45, 49, 51, 55, 57 of the struts 23, 29, 35, 41, 47, 53 to the second end portion 159 may vary as will now be apparent to those skilled in the art. Thus, for example, the respective ends 25, 27, 31, 33, 37, 39, 43, 45, 49, 51, 55, 57 of the struts 23, 29, 35, 41, 47, 53 may be externally threaded and each second end portion 159 may have a threaded aperture 163 for threadably receiving the respective ends 25, 27, 31, 33, 37, 39, 43, 45, 49, 51, 55, 57 of the struts 23, 29, 35, 41, 47, 53. The threaded aperture 163 may be formed in a tubular metal insert in each end portion 159 as will now be apparent to those skilled in the art.

Figure 19:
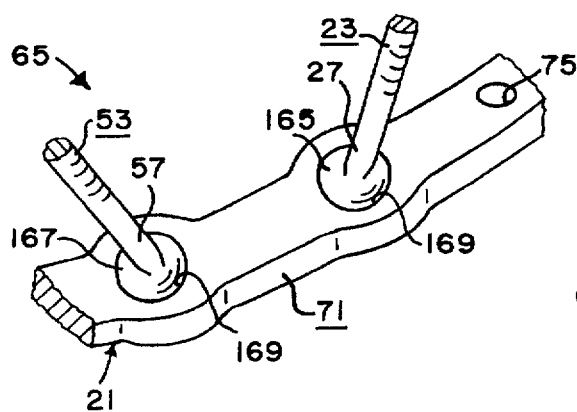
FIG. 19 is a perspective view of yet another modified embodiment of a connector means of the present invention.
Figure 20:
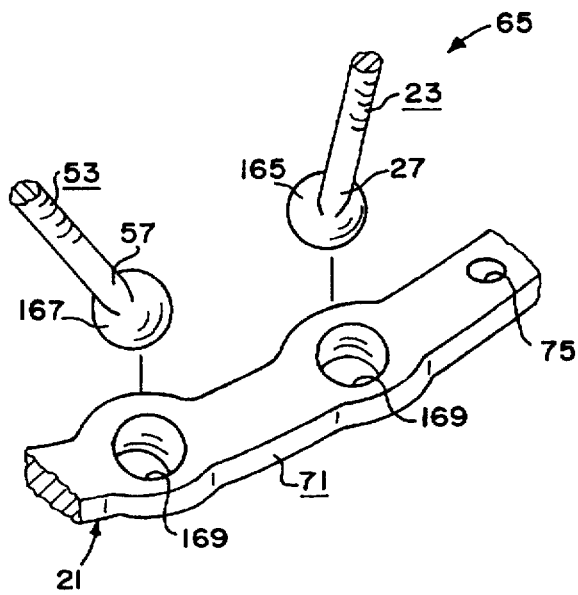
FIG. 20 is an exploded perspective view of FIG. 19.

In the embodiment shown in FIGS. 19 and 20, each of the connector means 59, 61, 63, 65, 67, 69 consists of a pair of spherical members. While only the connector means 65 is shown in FIGS. 19 and 20, the other connector means 59, 61, 63, 67, 69 are preferably similar or identical in construction thereto. The connector means as shown in FIGS. 19 and 20 includes a first spherical member 165 attached to one of the ends 25, 27, 31, 33, 37, 39, 43, 45, 49, 51, 55, 57 of one of the struts 23, 29, 35, 41, 47, 53, and a second spherical member 167 attached to another of the ends 25, 27, 31, 33, 37, 39, 43, 45, 49, 51, 55, 57 of one of the struts 23, 29, 35, 41, 47, 53. FIGS. 19 and 20 show the first spherical member 165 attached to the end 27 of the strut 23 and the second spherical member 167 attached to the end 57 of the strut 53. With respect to the embodiment shown in FIGS. 19 and 20, each ring 71 of each base member 19, 21 has a plurality of partially spherical cavities 169 sized and designed for rotatably entrapping one of the spherical members 165, 167. The partially spherical cavities 169 may be formed integrally with the rings 71 as shown clearly in FIGS. 19 and 20. On the other hand, each partially spherical cavity 169, or a coacting pair of partially spherical cavities 169, may be formed in a plate member 170 that can be bolted or otherwise fixedly attached to one of the rings 71 as clearly shown in FIG. 26 and as will now be apparent to those skilled in the art. Additional, each partially spherical cavity 169 may be partially formed in the rings 71 and partially formed in separate plate members which coact with one another to define the partially spherical cavities 169, etc.

Figure 21:
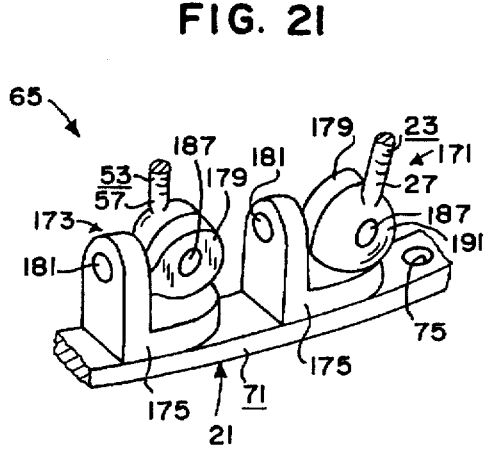
FIG. 21 is a perspective view of yet another modified embodiment of a connector means of the present invention.
Figure 22:
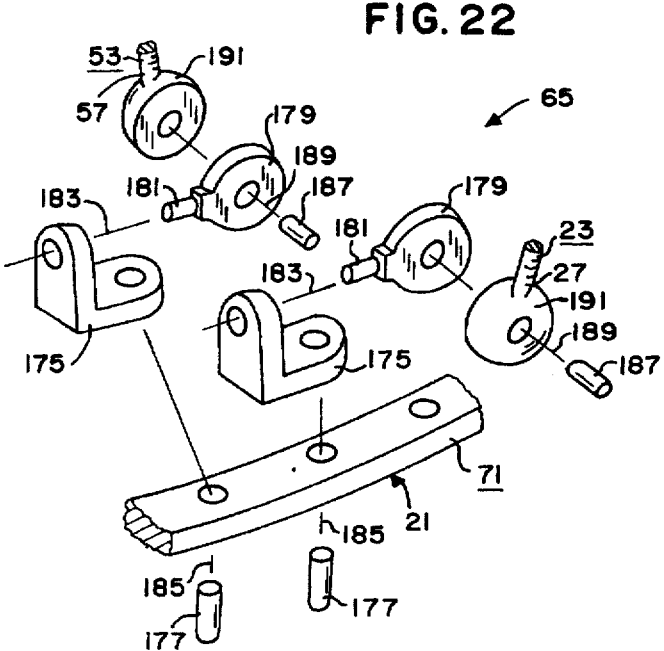
FIG. 22 is an exploded perspective view of FIG. 21.

In the embodiment shown in FIGS. 21 and 22, each of the connector means 59, 61, 63, 65, 67, 69 consists of a pair of U-joint type connectors. While only the connector means 65 is shown in FIGS. 21 and 22, the other connector means 59, 61, 63, 67, 69 are preferably similar or identical in construction thereto. The U-joint type connectors as shown in FIGS. 21 and 22 includes a first U-joint connector 171 attached to a respective one of the first and second base members 19, 21 and to one of the ends 25, 27, 31, 33, 37, 39, 43, 45, 49, 51, 55, 57 of one of the struts 23, 29, 35, 41, 47, 53, and a second U-joint connector 173 attached to the respective one of the first and second base members 19, 21 adjacent and independently of the first second U-joint connector 171 and to one of the ends 25, 27, 31, 33, 37, 39, 43, 45, 49, 51, 55, 57 of another of the struts 23, 29, 35, 41, 47, 53. Each U-joint connector 171, 173 preferably includes a first member 175, a shaft member 177 for attaching the first member 175 to a respective one of the base members 19, 21, a second member 179, a pivot member 181 for pivotally attaching the second member 179 to the first member 175 with the longitudinal axis 183 of the pivot member 181 extending transverse to the longitudinal axis 185 of the shaft member 177, and a pivot member 187 for pivotally attaching one of the ends 25, 27, 31, 33, 37, 39, 43, 45, 49, 51, 55, 57 of one of the struts 23, 29, 35, 41, 47, 53 to the second member 179 with the longitudinal axis 189 of the pivot member 187 extending transverse to the longitudinal axis 183 of the pivot member 181. The ends 25, 27, 31, 33, 37, 39, 43, 45, 49, 51, 55, 57 of the struts 23, 29, 35, 41, 47, 53 may include enlarged heads 191 through which the pivot member 187 extend as indicated in FIGS. 21 and 22. The shaft member 177 may be bolted or press-fitted or otherwise securely attached to the first member 175 or may be formed as an integral, one-piece unit with the first member 175, or may be rotatably secured to the respective base member 19, 21 by a typical retainer clip or the like as will now be apparent to those skilled in the art for pivotally attaching the first member 175 to a respective one of the base members 19, 21. The pivot member 181 may be press-fitted or otherwise securely attached to the second member 179 or may be formed as an integral, one-piece unit with the second member 179, and may be rotatably secured to the first member 175 by a typical retainer clip or the like as will now be apparent to those skilled in the art. The pivot member 187 may be press-fitted or otherwise securely attached to one of the coacting members (i.e., the second member 179 or the respective enlarged head 191) or may be formed as an integral, one-piece unit with one of the coacting members (i.e., the second member 179 or the respective enlarged head 191), or may be rotatably secured relative to each coacting member (i.e., to the second member 179 and the respective enlarged head 191) by typical retainer clips or the like as will now be apparent to those skilled in the art.

Figure 23:
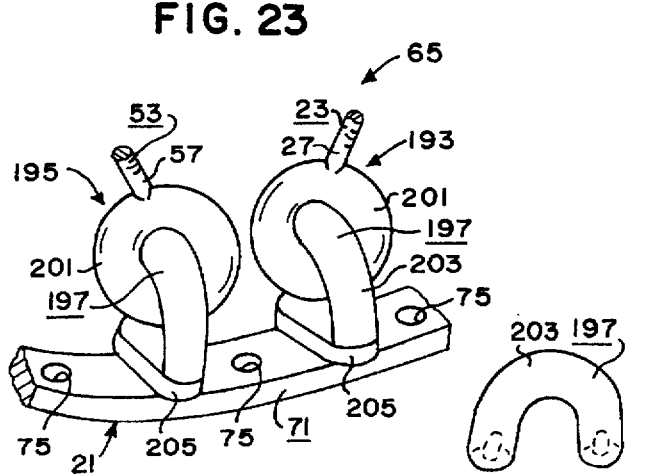
FIG. 23 is a perspective view of yet another modified embodiment of a connector means of the present invention.
Figure 24:
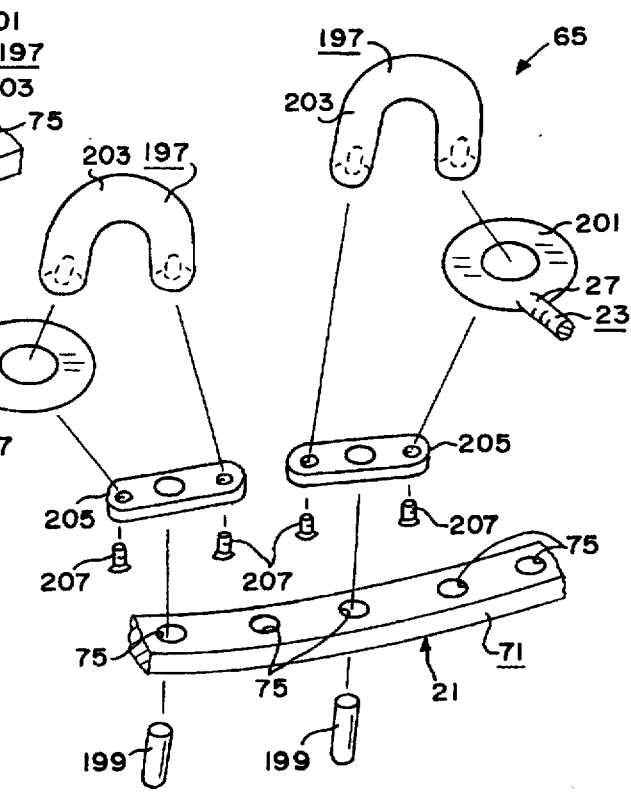
FIG. 24 is an exploded perspective view of FIG. 23.

In the embodiment shown in FIGS. 23 and 24, each of the connector means 59, 61, 63, 65, 67, 69 consists of a pair of chain link connectors. While only the connector means 65 is shown in FIGS. 23 and 24, the other connector means 59, 61, 63, 67, 69 are preferably similar or identical in construction thereto. The chain link connectors as shown in FIGS. 23 and 24 includes a first chain link connector 193 attached to a respective one of the first and second base members 19, 21 and to one of the ends 25, 27, 31, 33, 37, 39, 43, 45, 49, 51, 55, 57 of one of the struts 23, 29, 35, 41, 47, 53, and a second chain link connector 195 attached to the respective one of the first and second base members 19, 21 adjacent and independently of the first chain link connector 193 and to one of the ends 25, 27, 31, 33, 37, 39, 43, 45, 49, 51, 55, 57 of another of the struts 23, 29, 35, 41, 47, 53. Each chain link connector 193, 195 preferably includes a first ring member 197, a pivot member 199 pivotally attaching the first ring member 197 to a respective one of the first and second base members 19, 21, a second ring member 201 attached to one of the ends 25, 27, 31, 33, 37, 39, 43, 45, 49, 51, 55, 57 of one of the struts 23, 29, 35, 41, 47, 53 (the second ring member 201 of the first chain link connector 193 is shown in FIGS. 23 and 24 attached to the end 27 of the strut 23; the second ring member 201 of the second chain link connector 195 is shown in FIGS. 23 and 24 attached to the end 57 of the strut 53) and pivotally attached to the first ring member 197. Each first ring member 197 is preferably formed by a U-shaped member 203 for extending through the second ring member 201, and a bridge member 205 for closing the U-shaped member 203 after the U-shaped member 203 is passed through the central hole in the second member 201. The bridge member 205 may be removably attached to the U-shaped member 203 by screws 207 or the like (see FIG. 24). The pivot member 199 may be press-fitted or otherwise securely attached to the bridge member 205 or may be formed as an integral, one-piece unit with the bridge member 205, or may be rotatably secured to both the bridge member 205 and the respective base member 19, 21 by typical retainer clips or the like as will now be apparent to those skilled in the art. The method of attaching the second ring member 201 to the respective ends 25, 27, 31, 33, 37, 39, 43, 45, 49, 51, 55, 57 of the struts 23, 29, 35, 41, 47, 53 may vary as will now be apparent to those skilled in the art. Thus, for example, each ring member 201 may be integrally formed as a one-piece unit with a respective end 25, 27, 31, 33, 37, 39, 43, 45, 49, 51, 55, 57 of a respective strut 23, 29, 35, 41, 47, 53 as will now be apparent to those skilled in the art.

In the embodiment shown in FIG. 27, each adjustable effective length strut 23, 29, 35, 41, 47, 53 may consist of a one-piece, integral rod 209 having one end 211 with left hand external threads thereon, having another end 213 with right hand external threads thereon, and each connector means 59, 61, 63, 65, 67, 69 may have an appropriately handed threaded aperture 215 for screwably receiving one of the ends 211,213 of one of the rods 209. While only the connector means 59, 65 are shown in FIG. 27, the other connector means 61, 63, 67, 69 may be similar or identical in construction thereto. Likewise, while only portions of the struts 23, 29, 53 are shown in FIG. 27, the other struts 35, 41, 47 may be similar or identical in construction thereto. Each rod 209 may include grip means between the opposite ends to aid in the rotation thereof about its longitudinal axis. The grip means may consist simply of a transverse aperture 217 through the rod 209 to allow a bar or the like (not shown) to be inserted therethrough to provide a handle to allow the rod 209 to be easily rotated about its longitudinal axis as will now be apparent to those skilled in the art. The midportion of each rod 209 may be enlarged, etc., adjacent the transverse aperture 217 for reinforcement, etc. When a rod 209 is rotated, the associated connector means 59, 61, 63, 65, 67, 69 on the opposite ends thereof will move toward or away from one another, causing the effective length of the rod 209 to be varied and causing a corresponding or related movement of the base members 19, 21 as will now be apparent to those skilled in the art. It should also be noted that while FIG. 27 shows the split-ball connectors of FIGS. 1–7 and 10, it is not limited thereto and may be used with the type connectors shown in FIGS. 11–24, etc.

Figure 28:
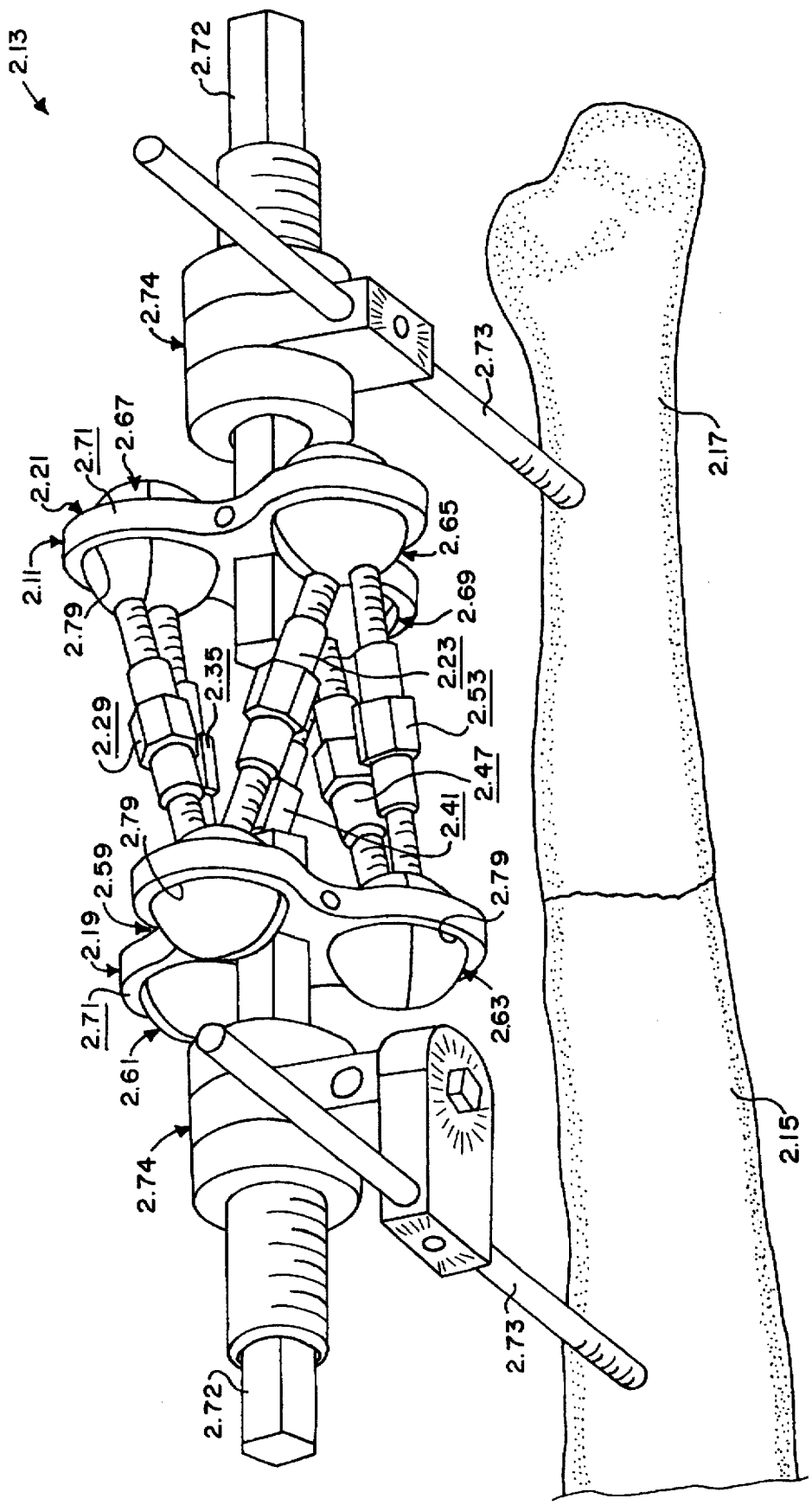
FIG. 28 is a perspective view of a second preferred embodiment of the of the present invention shown in combination with other elements of an orthopedic external fixator and a fractured tibia.

A second preferred embodiment of the present invention is shown in FIG. 28, and identified by the numeral 2.11. The external fixator 2.11 is a concentric part of a unilateral-type orthopedic external fixator 2.13 for securing a first bone element 2.15 relative to a second bone element 2.17.

The external fixator 2.11 includes a first base member 2.19 for attachment to the first bone element 2.15; a second base member 2.21 for attachment to the second bone element 2.17; an adjustable effective length first strut 2.23 having a first end and a second end; an adjustable effective length second strut 2.29 having a first end and a second end; an adjustable effective length third strut 2.35 having a first end and a second end; an adjustable effective length fourth strut 2.41 having a first end and a second end; an adjustable effective length fifth strut 2.47 having a first end and a second end; an adjustable effective length sixth strut 2.53 having a first end and a second end; first connector means 2.59 for rotatably attaching the first ends of the first and second struts 2.23, 2.29 to one another and relative to the first base member 2.19; second connector means 2.61 for rotatably attaching the first ends of the third and fourth struts 2.35, 2.41 to one another and relative to the first base member 2.19; third connector means 2.63 for rotatably attaching the first ends of the fifth and sixth struts 2.47, 2.53 to one another and relative to the first base member 2.19; fourth connector means 2.65 for rotatably attaching the second ends of the first and sixth struts 2.23, 2.53 to one another and relative to the second base member 2.21; fifth connector means 2.67 for rotatably attaching the second ends of the second and third struts 2.29, 2.35 to one another and relative to the second base member 2.21; and sixth connector means 2.69 for rotatably attaching the second ends of the fourth and fifth struts 2.41, 2.47 to one another and relative to the second base member 2.21.

The first and second base members 2.19, 2.21 may be constructed in various manners, out of various materials, and in various shapes and sizes. Thus, for example, each base member 2.19, 2.21 may consist of a one-piece or multi-piece plate 2.71 for being concentrically secured to a rigid elongated rod 2.72 or the like by way of typical set screws or the like. Standard transfixation screws, wires or pins 2.73, etc., are coupled relative to the base members 2.19, 2.21 and rods 2.72 by various connectors 2.74 which may be mounted on or an integral part of the plates 2.71, or may be mounted directly on the rods 2.72 as shown in FIG. 28 and as will now be apparent to those skilled in the art.

The struts 2.23, 2.29, 2.35, 2.41, 2.47, 2.53 and connector means 2.59, 2.61, 2.63, 2.65, 2.67, 2.69 are preferably identical to the various struts 23, 29, 35, 41, 47, 53 and connectors means 59, 61, 63, 65, 67, 69 discloses hereinabove relative to the frame 11 and reference should be made to the detailed disclosure hereinabove of the various struts 23, 29, 35, 41, 47, 53 and connectors means 59, 61, 63, 65, 67, 69 for a complete understanding of the various possible constructions of the struts 2.23, 2.29, 2.35, 2.41, 2.47, 2.53 and connector means 2.59, 2.61, 2.63, 2.65, 2.67, 2.69 of the frame 2.11. Each plate 2.71 is constructed for use with the connector means 2.59, 2.61, 2.63, 2.65, 2.67, 2.69 used. Thus, for example, with respect to the embodiment shown in FIG. 28, each plate 2.71 preferably has a plurality of partially spherical cavities 2.79 therein for rotatably entrapping a respective pair of the partially spherical members of the split-ball connector means shown.

Figure 29:
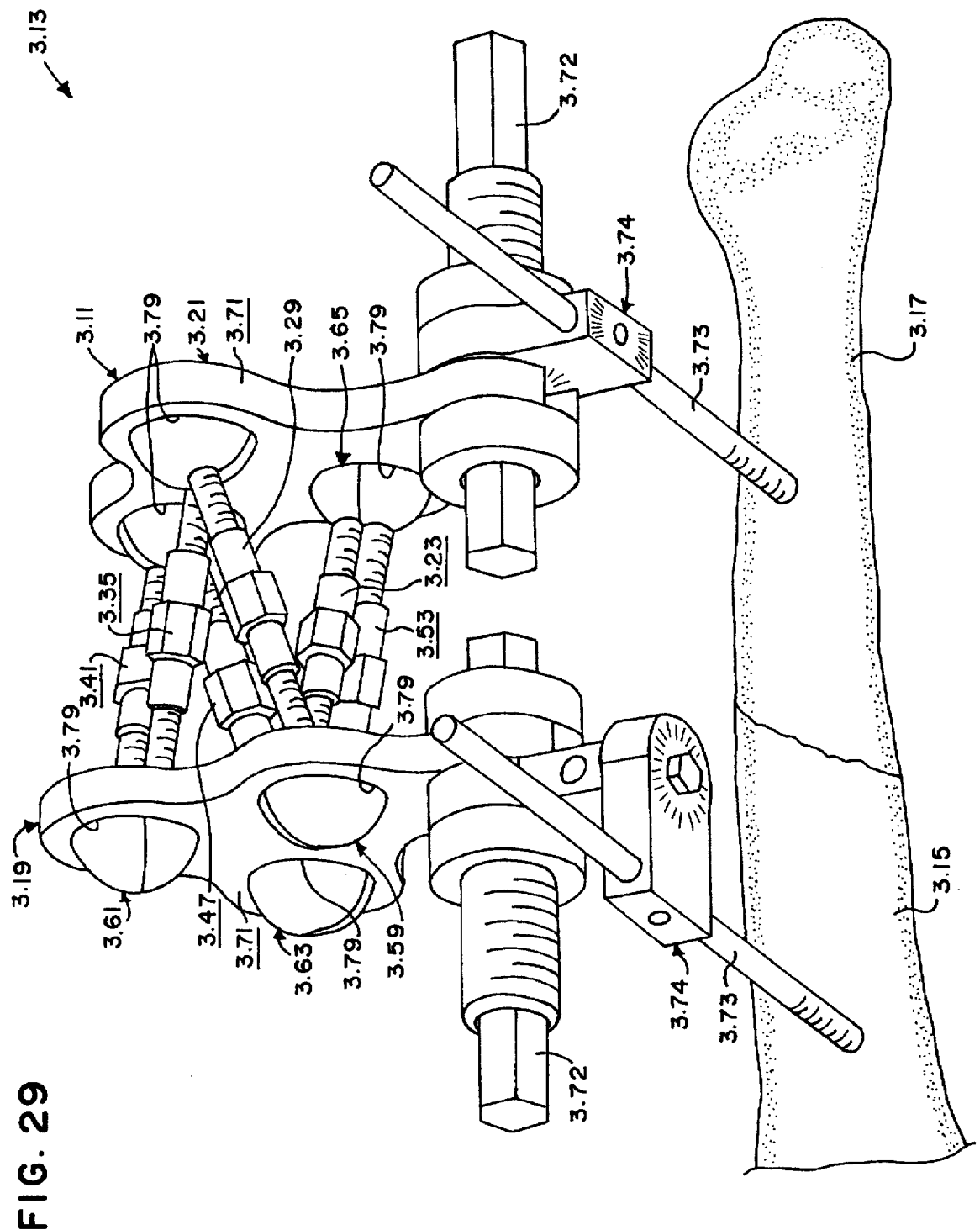
FIG. 29 is a perspective view of a third preferred embodiment of the present invention shown in combination with other elements of an orthopedic external fixator and a fractured tibia.

A third preferred embodiment of the present invention is shown in FIG. 29, and identified by the numeral 3.11. The spatial frame 3.11 is part of a eccentrically mounted, unilateral-type orthopedic external fixator 3.13 for securing a first bone element 3.15 relative to a second bone element 3.17.

The external fixator 3.11 includes a first base member 3.19 for attachment to the first bone element 3.15; a second base member 3.21 for attachment to the second bone element 3.17; an adjustable effective length first strut 3.23 having a first end and a second end; an adjustable effective length second strut 3.29 having a first end and a second end;

an adjustable effective length third strut 3.35 having a first end and a second end; an adjustable effective length fourth strut 3.41 having a first end and a second end; an adjustable effective length fifth strut 3.47 having a first end and a second end; an adjustable effective length sixth strut 3.53 having a first end and a second end; first connector means 3.59 for rotatably attaching the first ends of the first and second struts 3.23, 3.29 to one another and relative to the first base member 3.19; second connector means 3.61 for rotatably attaching the first ends of the third and fourth struts 3.35, 3.41 to one another and relative to the first base member 3.19; third connector means 3.63 for rotatably attaching the first ends of the fifth and sixth struts 3.47, 3.53 to one another and relative to the first base member 3.19; fourth connector means 3.65 for rotatably attaching the second ends of the first and sixth struts 3.23, 3.53 to one another and relative to the second base member 3.21; fifth connector means 3.67 for rotatably attaching the second ends of the second and third struts 3.29, 3.35 to one another and relative to the second base member 3.21; and sixth connector means 3.69 for rotatably attaching the second ends of the fourth and fifth struts 3.41, 3.47 to one another and relative to the second base member 3.21.

The first and second base members 3.19, 3.21 may be constructed in various manners, out of various materials, and in various shapes and sizes. Thus, for example, each base member 3.19, 3.21 may consist of a one-piece or multi-piece plate 3.71 for being eccentrically secured to a rigid elongated rod 3.72 or the like by way of typical set screws or the like. Standard transfixation screws, wires or pins 3.73, etc., are coupled relative to the base members 3.19, 3.21 and rods 3.72 by various connectors 3.74 which may be mounted on or an integral part of the plates 3.71, or may be mounted directly on the rods 3.72 as shown in FIG. 29 and as will now be apparent to those skilled in the art.

The struts 3.23, 3.29, 3.35, 3.41, 3.47, 3.53 and connector means 3.59, 3.61, 3.63, 3.65, 3.67, 3.69 are preferably identical to the various struts 23, 29, 35, 41, 47, 53 and connectors means 59, 61, 63, 65, 67, 69 discloses hereinabove relative to the frame 11 and reference should be made to the detailed disclosure hereinabove of the various struts 23, 29, 35, 41, 47, 53 and connectors means 59, 61, 63, 65, 67, 69 for a complete understanding of the various possible constructions of the struts 3.23, 3.29, 3.35, 3.41, 3.47, 3.53 and connector means 3.59, 3.61, 3.63, 3.65, 3.67, 3.69 of the frame 3.11. Each plate 3.71 is constructed for use with the connector means 3.59, 3.61, 3.63, 3.65, 3.67, 3.69 used. Thus, for example, with respect to the embodiment shown in FIG. 29, each plate 3.71 preferably has a plurality of partially spherical cavities 3.79 therein for rotatably entrapping a respective pair of the partially spherical members of the split-ball connector means shown.

As thus constructed, the present invention provides a novel external fixator and repositioning mechanism. The fixator preferably includes two base members or swash plates coupled together by six struts which are adjustable in length. These struts in their resting positions are inclined with respect to one another. In the preferred embodiments, these struts are regularly spaced and similar in manufacture to aid in construction and clinical use, although irregular arrays of dissimilarly constructed struts could effect a gradual six axis correction. Each strut of one preferred embodiment is essentially a turnbuckle attached to a half sphere at either end. One half sphere is mated to a half sphere of an adjacent strut in a partially encapsulating socket, there being three such sockets on each of the swash plates. The sockets of one swash plate may be staggered with respect to the sockets of the other swash plate when viewed axially. The partial sockets which constrain the split balls may be an integral part of the swash plates or may be attached additionally. The present invention functions as a frame and a mechanism without the sockets actually clamping the balls against rotation. Ideally there is sufficient clearance to allow rotation of the balls about three axes and each half spheres about an axis perpendicular to the face of each half sphere, passing through the centers of the hemispheres without allowing excessive play along the three translational axes. Additional clamping of the balls could be done to prevent motion, but the present device is able to function as a repositioning mechanism by virtue of the changing length of the struts and therefore a concomitant rotation of half spheres about each other and/or the ball joint pair within their sockets. The present device can function as a stabilizing frame even though the balls are not tightly clamped but free to rotate. External fixation pin clamps may either be an integral part of the swash plates or may be attached. These clamps are then attached to pins or wires which are attached to bone fragments. Bone fragment positions may be changed by adjusting the effective lengths of the six struts accordingly. Each new six coordinate position of one fragment relative to the other can be achieved by changing the effective lengths of the six struts. Each combination of strut lengths determines a unique six coordinate position of one fragment relative to the other. No change in position between fragments can occur unless there is a change in the effective length of one or more struts. There is no over constraint, in that any change of any strut length causes a change in position of one fragment with respect to the other. The exact change in length for each strut to move one fragment relative to the other a prescribed amount can be accomplished by coordinate transformation by hand calculation, calculator, or computer. Alternatively, similar accessory swash plates with only the centers of the split balls represented can be utilized to determine initial lengths of the struts. Orthogonal x-rays of a deformed limb are taken, and these, plus careful physical examination, are used to characterize or measure a deformity. In its deformed position, one fragment can be thought of as moved from its original or preferred position by displacement along and/or about the six axes which can be corrected by the present external fixator. Assuming a neutral or home position of the present invention, the accessory swash plates are held in a similar home position. One accessory swash plate is then displaced from the other accessory swash plate along and/or about the six axes in an amount equal to the deformities as measured on x-ray and physical exam. While the accessory swash plates are held in this deformed spatial relationship the distance between marks corresponding to the centers of the split ball joints are measured. The corresponding strut is then adjusted to match. This is repeated for the remaining five strut lengths. At the end of this process the present invention is deformed exactly as the limb. The present invention is then securely attached to the bone fragments with skeletal pins or wires. The struts are then gradually or suddenly adjusted to their original or home length. The boney deformity is corrected as the present invention is corrected since the present invention is attached to the bone.

Although the present invention has been described and illustrated with respect to preferred embodiments thereof and preferred uses therefor, it is not to be so limited since modifications and changes can be made therein which are within the full intended scope of the invention.

We claim:

1. An orthopedic fixator for positioning a first element relative to a second element, said fixator comprising:

(a) a first base member for mounting to said first element;

(b) a second base member for mounting to said second element;

(c) an adjustable effective length first strut having a first end and a second end;

(d) an adjustable effective length second strut having a first end and a second end;

(e) an adjustable effective length third strut having a first end and a second end;

(f) an adjustable effective length fourth strut having a first end and a second end;

(g) an adjustable effective length fifth strut having a first end and a second end;

(h) an adjustable effective length sixth strut having a first end and a second end;

(i) first connector for rotatably attaching said first ends of said first and second struts relative to one another and relative to said first base member;

(j) second connector for rotatably attaching said first ends of said third and fourth struts relative to one another and relative to said first base member;

(k) third connector for rotatably attaching said first ends of said fifth and sixth struts relative to one another and relative to said first base member;

(l) fourth connector for rotatably attaching said second ends of said first and sixth struts relative to one another and relative to said second base member;

(m) fifth connector for rotatably attaching said second ends of said second and third struts relative to one another and relative to said second base member; (n) sixth connector for rotatably attaching said second ends of said fourth and fifth struts relative to one another and relative to said second base member.

2. The orthopedic fixator of claim 1 in which said first connector includes first and second partially spherical members, said second connector includes third and fourth partially spherical members, said third connector includes fifth and sixth partially spherical members, said forth connector includes seventh and eight partially spherical members, said fifth connector includes ninth and tenth partially spherical members, said sixth connector includes eleventh and twelfth partially spherical members; and said first partially spherical member is attached to said first end of said first strut, said second partially spherical member is attached to said first end of said second strut, said third partially spherical member is attached to said first end of said third strut, said fourth partially spherical member is attached to said first end of said fourth strut, said fifth partially spherical member is attached to said first end of said fifth strut, said sixth partially spherical member is attached to said first end of said sixth strut, said seventh partially spherical member is attached to said second end of said first strut, said eight partially spherical member is attached to said second end of said second strut, said ninth partially spherical member is attached to said second end of said third strut, said tenth partially spherical member is attached to said second end of said fourth strut, said eleventh partially spherical member is attached to said second end of said fifth strut, said twelfth partially spherical member is attached to said second end of said sixth strut; and in which said first base member has a first partially spherical cavity for rotatably entrapping said first and second partially spherical members, a second partially spherical cavity for rotatably entrapping said third and fourth partially spherical members, and a third partially spherical cavity for rotatably entrapping said fifth and sixth partially spherical members: and in which said second base member has a fourth partially spherical cavity for rotatably entrapping said seventh and eight partially spherical members, a fifth partially spherical cavity for rotatably entrapping said ninth and tenth partially spherical members, and a sixth partially spherical cavity for rotatably entrapping said eleventh and twelfth partially spherical members.

3. The orthopedic fixator of claim 2 in which each of said partially spherical members has a face portion; and in which said face portions of said first and second partially spherical members are held movably against one another, said face portions of said third and fourth partially spherical members are held movably against one another, said face portions of said fifth and sixth partially spherical members are held movably against one another, said face portions of said seventh and eight partially spherical members are held movably against one another, said face portions of said ninth and tenth partially spherical members are held movably against one another, said face portions of said eleventh and twelfth partially spherical members are held movably against one another.

4. The orthopedic fixator of claim 3 in which each of said connectors includes a pivot member extending through the center of each of said face portions of a coacting pair of said partially spherical members for pivotally joining that pair of said partially spherical members to one another.

5. The spatial frame of claim 1 in which each of said connector means includes:

(a) a first member, (b) a first pivot member pivotally attaching said first member to a respective one of said first and second base members, said first pivot member having a longitudinal axis, (c) a second member, (d) a second pivot member pivotally attaching said second member to said first member, said second pivot member having a longitudinal axis extending transverse to said longitudinal axis of said first pivot member, and (e) a third pivot member pivotally attaching one of said ends of one of said struts and one of said ends of another of said struts to said second member, said third pivot member having a longitudinal axis extending transverse to said longitudinal axis of said second pivot member.

6. The orthopedic fixator of claim 1 in which each of said connectors includes:

(a) a first ring member pivotally attached to a respective one of said first and second base members;

(c) a second ring member attached to one of said ends of one of said struts and pivotally attached to said first ring member; and (d) a third ring member attached to one of said ends of another of said struts and pivotally attached to said first ring member.

7. The orthopedic fixator of claim 1 in which each of said connectors includes a body for attachment to a respective one of said base members, to one of said ends of one of said struts, and to one of said ends of another of said struts: said body being elastic for allowing pivotal movement of said struts relative to said base members.

8. The orthopedic fixator of claim 7 in which said body has a trunk portion for attachment to a respective one of said base members, has a first arm portion extending outward from said trunk portion for attachment to one of said ends of one of said struts, and has a second arm portion extending outward from said trunk portion for attachment to one of said ends of another of said struts.

9. The orthopedic fixator of claim 1 in which each of said connectors includes a first body for attachment to a respective one of said base members and to one of said ends of one of said struts; in which each of said connectors includes a second body for attachment to a respective one of said base members adjacent said first body and to one of said ends of another of said struts; said first and second body being elastic for allowing pivotal movement of said struts relative to said base members.

10. The orthopedic fixator of claim 1 in which each of said struts includes a first component, a second component, and coupler for adjustably coupling said first and second components to one another.

11. The orthopedic fixator of claim 10 in which said first component includes an elongated rod having threaded end; in which said second component includes an elongated rod having a threaded end; and in which said coupler has a threaded portion for coacting with said threaded ends of said rods of said first and second components.

12. The orthopedic fixator of claim 11 in which said threaded portion of said coupler has a first end with right-hand threads and a second end with left-hand threads; in which said threaded end of said rod of said first component has right-hand threads for coacting with said first end of said threaded portion of said coupler; and in which said threaded end of said rod of said second component has left-hand threads for coacting with said second end of said threaded portion of said coupler.

13. The orthopedic fixator of claim 1 in which each of said base members include a ring member for encircling a portion of said elements.

14. The orthopedic fixator of claim 1 in which is included a first elongated rod and a second elongated rod; in which said first base member includes a plate member attached to said first elongated rod; and in which said second base member includes a plate member attached to said second elongated rod.

15. The orthopedic fixator of claim 14 in which said connectors connect said struts relative to said plate members of said base members with said struts mounted concentrically to said longitudinal axes of said first and second elongated rods.

16. The orthopedic fixator of claim 14 in which said connectors connect said struts relative to said plate members of said base members with said struts mounted eccentrically to said longitudinal axes of said first and second elongated rods.

17. An orthopedic fixator for securing a first bone element relative to a second bone element, said fixator comprising:

(a) a first base member for attachment to said first bone element;

(b) a second base member for attachment to said second bone element;

(c) an adjustable effective length first strut having a longitudinal axis, having a first end, and having a second end;

(d) an adjustable effective length second strut having a longitudinal axis, having a first end, and having a second end;

(e) an adjustable effective length third strut having a longitudinal axis, having a first end, and having a second end;

(f) an adjustable effective length fourth strut having a longitudinal axis, having a first end, and having a second end;

(g) an adjustable effective length fifth strut having a longitudinal axis, having a first end, and having a second end;

(h) an adjustable effective length sixth strut having a longitudinal axis, having a first end, and having a second end; and (i) a plurality of connectors for rotationally movably connecting said first ends of said struts to said first base member and said second ends of said struts to said second base member, for allowing free unclamped rotation of said first ends of said struts relative to said first base member and said second ends of said struts relative to said second base member, and for preventing translation of said first ends of said struts away from said first base member and said second ends of said struts away from said second base member, for angling said longitudinal axis of said first strut to said longitudinal axis of said second strut, for angling said longitudinal axis of said second strut to said longitudinal axis of said third strut, for angling said longitudinal axis of said third strut relative to said longitudinal axis of said fourth strut, for angling said longitudinal axis of said fourth strut to said longitudinal axis of said fifth strut, for angling said longitudinal axis of said fifth strut relative to said longitudinal axis of said sixth strut, and for angling said longitudinal axis of said sixth strut relative to said longitudinal axis of said first strut.

18. An orthopedic fixator for securing a first bone element relative to a second bone element, said fixator comprising:

(a) a first base member for attachment to said first bone element;

(b) a second base member for attachment to said second bone element;

(c) an adjustable effective length first strut having a first end movably attached to said first base member and a second end movably attached to said second base member;

(d) an adjustable effective length second strut having a first end movably attached to said first base member and a second end movably attached to said second base member;

(e) an adjustable effective length third strut having a first end movably attached to said first base member and a second end movably attached to said second base member;

(f) an adjustable effective length fourth strut having a first end movably attached to said first base member and a second end movably attached to said second base member;

(g) an adjustable effective length fifth strut having a first end movably attached to said first base member and a second end movably attached to said second base member;

(h) an adjustable effective length sixth strut having a first end movably attached to said first base member and a second end movably attached to said second base member;

in which said first ends of said first and second struts are joined relative to one another so that movement of said first end of one of said first and second struts will cause a corresponding movement of said first end of said other strut;

in which said first ends of said third and fourth struts are joined relative to one another so that movement of said first end of one of said third and fourth struts will cause a corresponding movement of said first end of said other strut; and in which said first ends of said fifth and sixth struts are joined relative to one another so that movement of said first end of one of said fifth and sixth struts will cause a corresponding movement of said first end of said other strut.

19. A orthopaedic fixator for selective repositioning of a first bone relative to a second bone, said device comprising:

(a) a first base member having a fastener that attaches said first bone to said first base member;

(b) a second base member having a fastener that attaches said second bone to said second base member;

(c) a plurality of adjustable effective length struts each having a first end and a second end, wherein the first end of each of said struts is pivotably connected to said first base member, and the second end of each of said struts is pivotably connected to said second base member;

whereby the effective length of one or more of said struts can be adjusted to adjust the translational position of said first bone relative to said second bone.

20. The device of claim 19 wherein the effective length of one or more struts can further be adjusted to rotate said first bone relative to said second bone.

21. The device of claim 19 wherein said device includes at least six adjustable effective length struts.

22. The device of claim 21 wherein said device includes a first, second, third, forth, fifth, and sixth connector, and a first, second, third, forth, fifth, and sixth strut; whereby the first connector pivotably connects the first ends of said first and second struts to said first base member, the second connector pivotably connects the first ends of said third and fourth struts to said first base member, the third connector pivotably connects the first ends of said fifth and sixth struts to said first base member, the fourth connector pivotably connects the second ends of said first and second struts to said second base member, the fifth connector pivotably connects the second ends of said third and fourth struts to said second base member, the sixth connector pivotably connects the second ends of said fifth and sixth struts to said second base member.

23. The device of claim 19 wherein said first and second base members are collars that extend around said first and second bones, respectively.

24. The device of claim 19 wherein said first and second base member fasteners are selected from the group consisting of screws, wires and pins.

25. The device of claim 19 wherein said struts each include an effective length adjustment mechanism selected from the group consisting of a turnbuckle.

26. A orthopaedic fixator for selective repositioning of a first bone relative to a second bone, said device comprising:

(a) a first base member having a fastener that attaches said first bone to said first base member;

(b) a second base member having a fastener that attaches said second bone to said second base member;

(c) at least six adjustable effective length struts each having a first end and a second end, wherein the first end of each of said struts is pivotably connected to said first base member, and the second end of each of said struts is pivotably connected to said second base member;

whereby the effective length of one or more of said struts can be changed to adjust the translational position of said first bone relative to said second bone or adjust the rotational position of said first bone relative to said second bone.

27. The device of claim 26 wherein said device includes a first, second, third, forth, fifth, and sixth connector, and a first, second, third, forth, fifth, and sixth strut; whereby the first connector pivotably connects the first ends of said first and second struts to said first base member, the second connector pivotably connects the first ends of said third and fourth struts to said first base member, the third connector pivotably connects the first ends of said fifth and sixth struts to said first base member, the fourth connector pivotably connects the second ends of said first and second struts to said second base member, the fifth connector pivotably connects the second ends of said third and fourth struts to said second base member, the sixth connector pivotably connects the second ends of said fifth and sixth struts to said second base member.

28. The device of claim 26 wherein said first and second base members are collars that extend around said first and second bones, respectively.

29. The device of claim 26 wherein said first and second base member fasteners are selected from the group consisting of screws, wires and pins.

30. The device of claim 26 wherein said struts each include an effective length adjustment mechanism selected from the group consisting of a turnbuckle.

* * * * *